(12) United States Patent
Chern

(10) Patent No.: US 7,365,231 B2
(45) Date of Patent: Apr. 29, 2008

(54) COMPOUND WITH ANTITUMOR ACTIVITY AND PREPARATION METHOD THEREFOR

(75) Inventor: Yaw-Terng Chern, Taipei (TW)

(73) Assignee: National Taiwan University of Science & Technology, Taipei (TW)

( * ) Notice: Subject to any disclaimer, the term of this patent is extended or adjusted under 35 U.S.C. 154(b) by 217 days.

(21) Appl. No.: 11/111,406

(22) Filed: Apr. 21, 2005

(65) Prior Publication Data

US 2006/0241187 A1 Oct. 26, 2006

(51) Int. Cl.
  C07C 215/26 (2006.01)
  C07C 215/28 (2006.01)
  C07C 317/14 (2006.01)
  C07C 205/06 (2006.01)
  A61K 31/05 (2006.01)

(52) U.S. Cl. .............. 564/315; 564/426; 564/428; 564/429; 564/440; 564/443; 568/30; 568/586; 514/648; 514/656; 514/657

(58) Field of Classification Search .............. None
See application file for complete search history.

(56) References Cited

OTHER PUBLICATIONS

Database CAPLUS on STN, Acc. No. 1994:164950, Winzeler et al., Polymer Preprints (ACS Division of Polymer Chemistry) (1993), 34(1), p. 425-6 (abstract).*
Database CAPLUS on STN, Acc. No. 2004:738900, Fujimoto et al., JP 2004250438 (Sep. 9, 2004) (abstact).*
Sherr, Charles J. , "Cancer Cell Cycles", Science, vol. 274: 1672-7 (Dec. 1996).
Aigami, Koji, Y. Inamoto, N. Takaishi and K. Hattori, "Biologically Active Polycycloalkanes. 1. Antiviral Adamantane Derivatives", J. Med. Chem., vol. 18: 713-21 (1975).
Tverdislov, V. A., et al., "Interaction of the Antivirus Agents Remantadine and Amantadine with Lipid Membranes and the Influence on the Curvature of Human Red Cells", Gen. Physiol. Biophys. 5, 61-75 (1986).
Komhuber, J., J. Bormann, M. Hubers, K. Rusche and P. Riederer, "Effects of the 1-amino-adamantanes at the MK-801-binding site of the NMDA-receptor-gated ion channel: a human postmortem brain study", European Journal of Pharmacology—Molecular Pharmacology Section, 206: 297-300 (1991).
Donath, Edwin, et al. "The Influence of the Antiviral Drugs Amantadine and Rimantadine on Erythrocyte and Platelet Membranes and its Comparison with that of Tetracaine", Biochemical Pharmacology 36:481-7 (1987).
Wang, J-J, Y-T Chern, Y-F Chang, T-Y Liu and C-W Chi, "Dimethyladamantylmaleimide-induced in vitro and in vivo growth inhibition of human colon cancer Colo205 cells", Anti-Cancer Drugs 13: 533-43 (2002).
Wang, J-J, Y-T Chern, Y-F Chang, T-Y Liu and C-W Chi, "In vitro and in vivo growth inhibition of cancer cells by adamantylmaleimide derivatives", Anti-Cancer Drug Design, 13: 779-796 (1998).
Wang, J-J, K-T Huang and Y-T Chern, "Induction Of Growth Inhibition And G1 Arrest in Human Cancer Cell Lines By Relatively Low-Toxic Diamantane Derivatives", Anti-Cancer Drugs 15:277-286 (2004).
Wang, J-J, Y-F Chang, Y-T Chern, and C-W Chi, "Study of in vitro and in vivo effects of 1,6Bis[4-(4-amino-3-hydroxyphenoxyl)phenyl]diamantane (DPD), a novel cytostatic and differentiation inducing agent, on human colon cancer cells", British Journal of Cancer, 89(10):1995-2003 (2003).
Attia, Mohammed A. M. and David W. Weiss, "Immunology of Spontaneous Mammary Carcinomas in Mice V. Acquired Tumor Resistance and Enhancement in Strain A Mice Infected with Mammary Tumor Virus", Cancer Research 26, Part 1: 1787-1800 (1966).
Wang, J-J, Y-C Chen, C-W Chi, K-T Huang and Y-T Chern, "In vitro and In vivo Growth Inhibition and G1 Arrest in Human Cancer Cells By Diaminophenyladamantane Derivatives", Anti-Cancer Drugs, 15: 697-705.

* cited by examiner

*Primary Examiner*—Brian Davis
(74) *Attorney, Agent, or Firm*—Volpe & Koenig PC

(57) ABSTRACT

The present invention provides the diaminophenyladamantane derivatives with antitumor activities and the preparation method therefore. The method includes a step of reacting an aromatic diol with at least one 5-halo-2-nitrophenol in the presence of at least one inorganic base in an organic solvent with a relatively high boiling point.

10 Claims, 7 Drawing Sheets

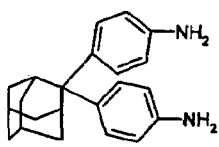

2,2-bis(4-aminophenyl)adamantane (2,2-DPANH$_2$) (NSC-711117)

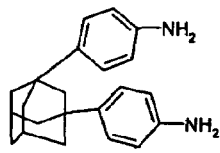

1,3-bis(4-aminophenyl)adamantane (1,3-DPANH$_2$) (NSC-711119)

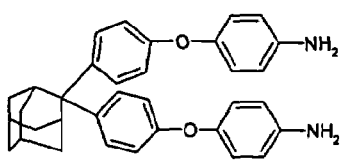

2,2-bis(4-(4-aminophenoxy)phenyl)adamantane (2,2-DPAONH$_2$)(NSC-711118)

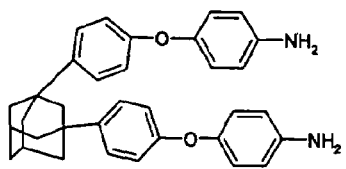

1,3-bis(4-(4-aminophenoxy)phenyl)adamantane (1,3-DPAONH$_2$)(NSC-706833)

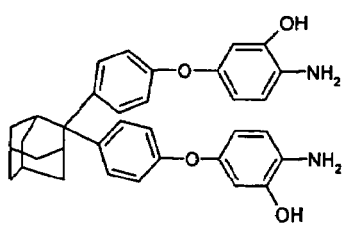

2,2-bis(4-(4-amino-3-hydroxyphenoxy)-phenyl)adamantane (DPA)(NSC-706832)

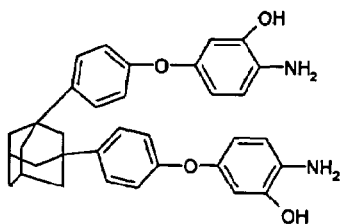

1,3-bis(4-(4-amino-3-hydroxyphenoxy)-phenyl)adamantane (1,3-DPA/OH/NH$_2$) (NSC-706835)

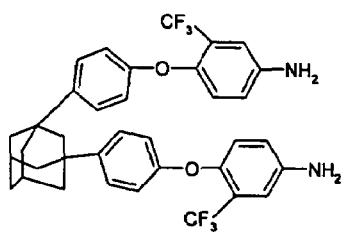

1,3-bis(4-(4-amino-2-trifluoromethylphenoxy)-phenyl)adamantane (1,3-DPA/CF$_3$/NH$_2$)(NSC-706834)

Fig. 1

COMPOUND WITH ANTITUMOR ACTIVITY AND PREPARATION METHOD THEREFOR

FIELD OF THE INVENTION

This invention relates to a composition with the antitumor activity, and more particularly to diaminophenyladamantane with antitumor activities and the preparation method therefor.

BACKGROUND OF THE INVENTION

Although chemotherapy and radiation therapy have been attempted in either adjuvant or palliative treatments, more effective adjuvant therapy is needed for colon cancer patients. Malignant tumor cells are clearly distinguished from normal cells by their chaotic proliferation due to a serious disorder of the cell cycle regulatory machinery. Cell cycle inhibitors or modulators that halt uncontrollable tumor growth are regarded as highly promising new therapeutic agents on human cancers. Recent studies have shown that the G1 phase of the cell cycle is an important period where various signals interact to determine the proliferation, quiescence, differentiation or apoptosis of cells (*Science* 1996; 274:1672-7). The use of chemical agents to induce differentiation of tumor cells has received widespread attention as a potentially less toxic cancer therapy.

Adamantane derivatives possess several attractive pharmacological activities such as antibacterial, antifungal, antiviral and anticancer effects (*J Med Chem* 1975; 18:713-21, *General Physiology & Biophysics* 1986; 5:61-75). Therefore, it is considered that the adamantane derivatives are highly promising candidates in drug design (*European Journal of Pharmacology* 1991; 206:297-300, *Biochemical Pharmacology* 1987; 36:481-7). For example, the aminoadamantane derivatives memantine (1-amino-3,5-dimethyl adamantane) and amantadine (1-aminoadamantane) are uncompetitive N-methyl-D-aspartate (NMDA) receptor antagonists which have been used clinically in the treatment of dementia and Parkinson's disease for several years without serious side effects (*European Journal of Pharmacology* 1991; 206:297-300, *Biochemical Pharmacology* 1987; 36:481-7). It is found in our previous study that N-1-adamantylmaleimide (AMI) and dimethyladamantylmaleimide (DMAMI) induce apoptosis and inhibit the growth of the human gastric (SC-M1) and colon (Colo 205) cancer in SCID mice, respectively (*Anti-Cancer Drugs* 2002; 13:533-43, *Anti-Cancer Drug Design* 1998; 13: 779-96). In a recent study, we have characterized the anticancer activities of diaminodiamantane derivatives from the 60 human cancer cell lines in NCI Anticancer Drug Screen, and evaluated the structure-activity relationship for the diaminodiamantane derivatives. It is found that 1,6-bis(4-(4-amino-3-hydroxyphenoxy)phenyl)diamantane (DPD) exhibited marked anticancer activities on the colon cancer cell lines (*Anti-cancer Drug* 2004; 15: 277-86). We have recently demonstrated that administration of DPD induced $G_0/G_1$ arrest and differentiation in human colon cancer cells (*Br. J Cancer* 2003; 89: 1995-2003). DPD also has in vivo anticancer activity on human colon cancer cells xenografts with no obvious acute toxicity.

Adamantane and diamantane are closely analogous polycyclic alkane with the structure of three and six fused cyclohexane rings, respectively. The present invention provides the preparation methods for the diaminophenyladamantane derivatives, including 1,3-bis(4-aminophenyl)adamantane (1,3-DPANH$_2$), 2,2-bis(4-aminophenyl)adamantane (2,2-DPANH$_2$), 1,3-bis(4-(4-aminophenoxy)phenyl)adamantane (1,3-DPAONH$_2$), 2,2-bis(4-(4-aminophenoxy)phenyl)adamantane (2,2-DPAONH$_2$), 1,3-bis-(4-(4-amino-3-hydroxyphenoxy)phenyl)adamantane (1,3-DPA/OH/NH$_2$), 2,2-bis(4-(4-amino-3-hydroxyphenoxy)phenyl)adamantane (DPA) and 1,3-bis-(4-(4-amino-2-trifluoromethylphenoxy)phenyl)adamantane (1,3-DPA/CF$_3$/NH$_2$). Furthermore, the diaminophenyladamantane derivatives in the present invention are verified to be with great antitumor activities.

SUMMARY OF THE INVENTION

It is an aspect of the present invention to provide a bis(o-nitrophenols) compound of a formula (I):

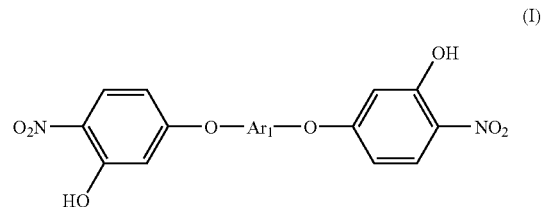

wherein Ar$_1$ is one selected from a group consisting of

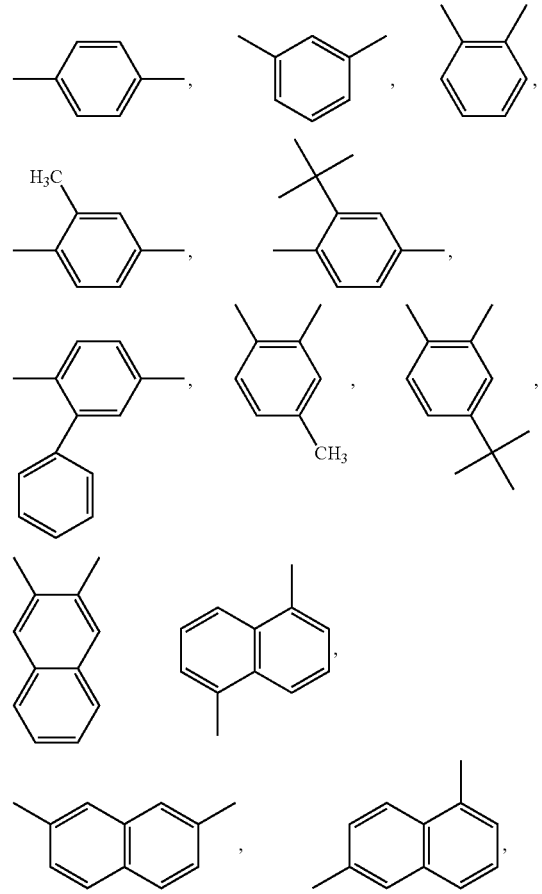

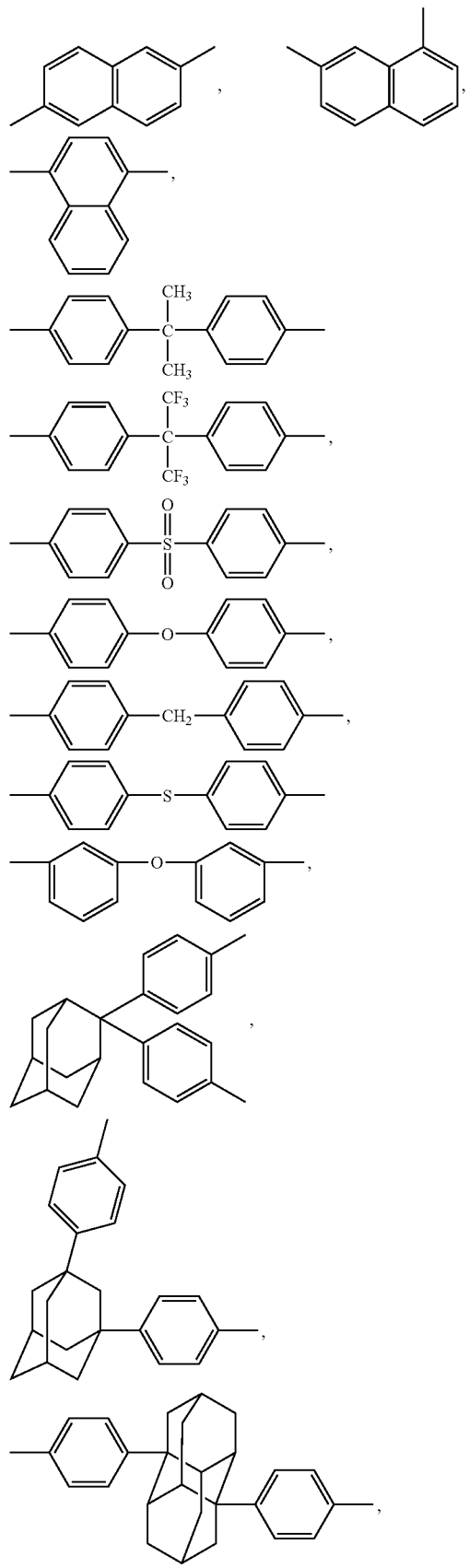
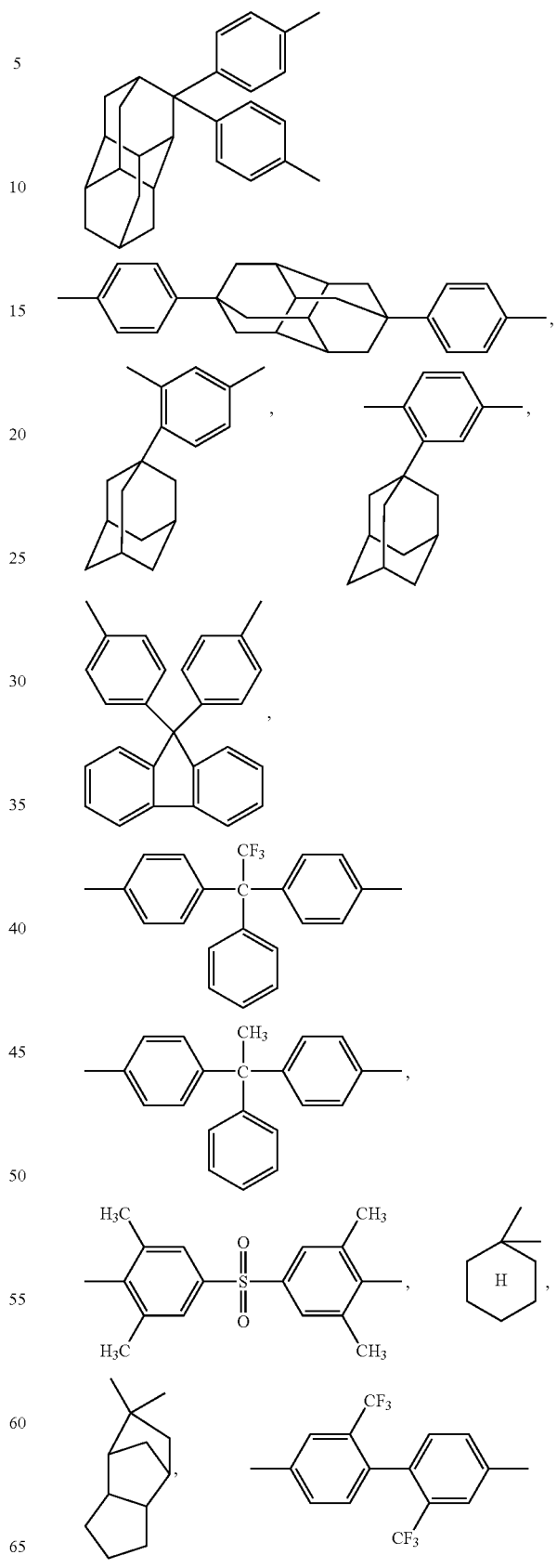

It is an aspect of the present invention to provide a bis(o-aminophenols) compound of a formula (II):

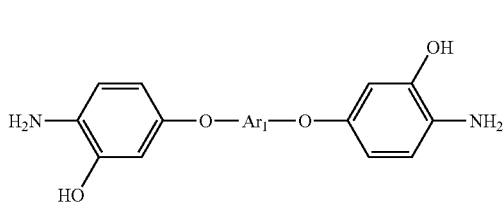

wherein $Ar_1$ is defined as the foregoing group.

It is an aspect of the present invention to provide a method for preparing the aforesaid formula (I). The method includes a step of reacting an aromatic diol with at least one 5-halo-2-nitrophenol in the presence of at least one inorganic base in an organic solvent with a relatively high boiling point, wherein the aromatic diol has a formula (III):

wherein $Ar_1$ is defined as the foregoing group.

In accordance with the present invention, the step is performed at a temperature ranged from 100 to 220° C., and an equivalent ratio of the inorganic base and the aromatic diol is less than 3.

In accordance with the present invention, the 5-halo-2-nitrophenol is one selected from a group consisting of 5-fluoro-2-nitrophenol, 5-chloro-2-nitrophenol, 5-bromo-2-nitrophenol and a combination thereof.

In accordance with the present invention, the organic solvent is one selected from a group consisting of N,N-dimethylformamide, N,N-dimethylacetamide, dimethyl sulfoxide, 1-methyl-2-pyrrolidone and a combination thereof.

In accordance with the present invention, the inorganic base is one selected from a group consisting of a carbonate salt, a hydroxide salt, a fluoride salt and a combination thereof.

It is an aspect of the present invention to provide a pharmaceutical composition for inhibiting a growth of tumor cells. The pharmaceutical composition includes a compound of the aforesaid formula (II).

In accordance with the present invention, the pharmaceutical composition further includes an irinotecan (CPT-11).

Preferably, the compound in the pharmaceutical composition is 2,2-bis(4-(4-amino-3-hydroxyphenoxy)phenyl)adamantane.

Preferably, the compound in the pharmaceutical composition is 1,3-bis(4-(4-amino-3-hydroxyphenoxy)phenyl)adamantane.

The above aspects and advantages of the present invention will become more readily apparent to those ordinarily skilled in the art after reviewing the following detailed description and accompanying drawings, in which:

BRIEF DESCRIPTION OF THE DRAWINGS

FIG. 1. shows the chemical structures of diaminophenyladamantane derivatives.

DETAILED DESCRIPTION OF THE PREFERRED EMBODIMENT

Figure 2A:
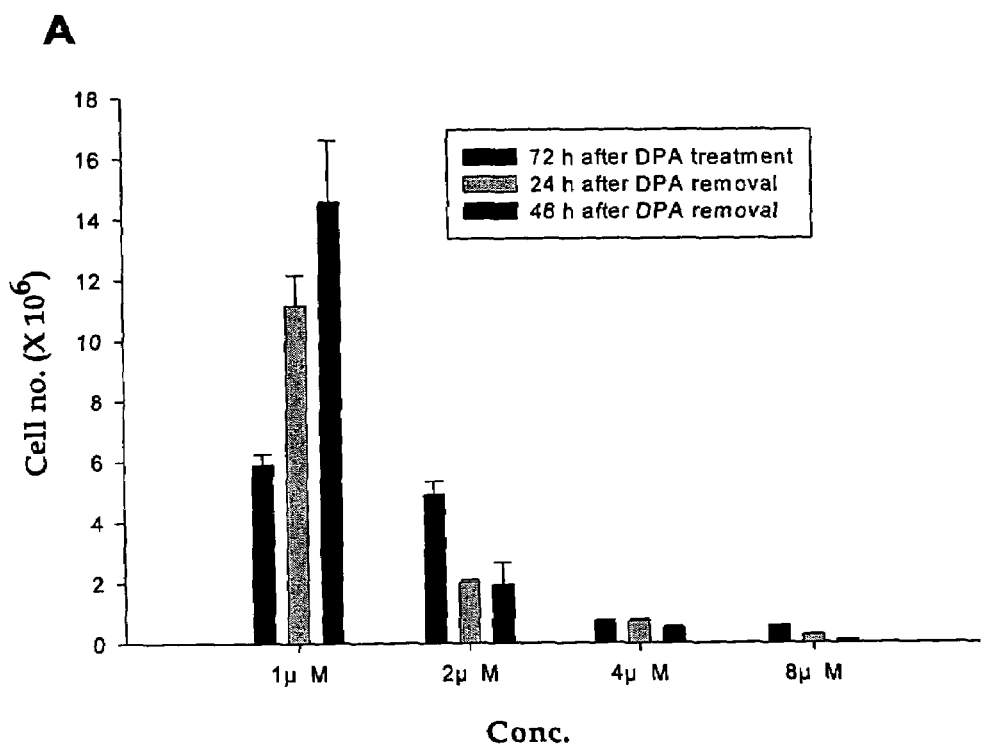
FIG. 2A is a chart showing the irreversible effect of DPA-induced growth inhibition of Colo 205.

The invention is described more specifically with reference to the following embodiments. It is to be noted that the following descriptions of preferred embodiments of this invention are presented herein for the purpose of illustration and description only; it is not intended to be exhaustive or to be limited to the precise form disclosed.

The present provides a method for preparing a compound of the formula (I):

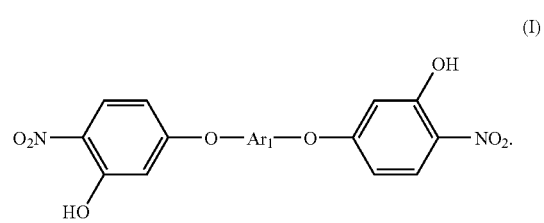

The method includes a step of reacting an aromatic diol with at least one 5-halo-2-nitrophenol in the presence of at least one inorganic base in an organic solvent with a relatively high boiling point, wherein the aromatic diol has a formula (III):

wherein $Ar_1$ is one selected from a group consisting of

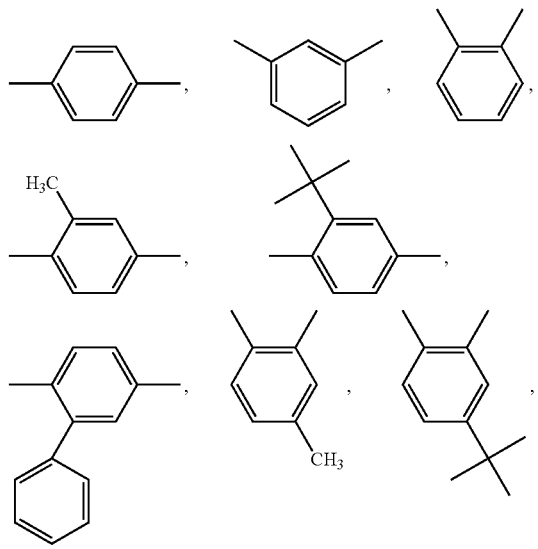

-continued
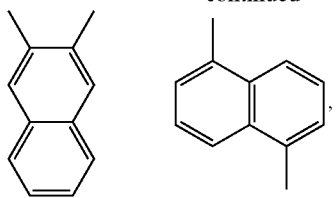
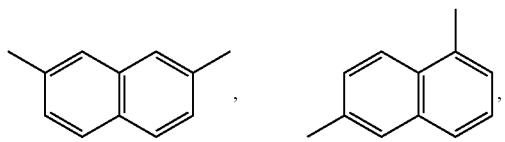
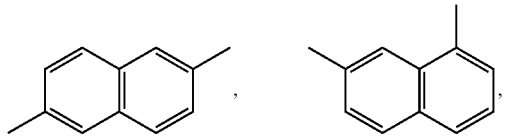
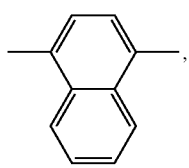
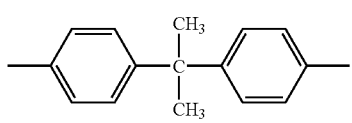
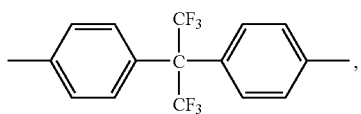
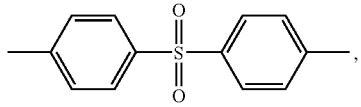
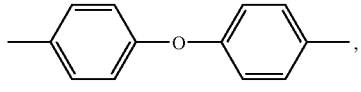
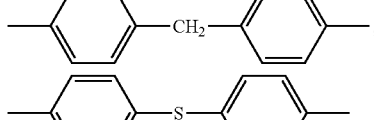
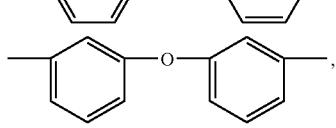
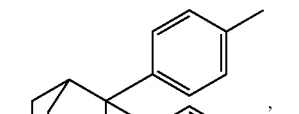
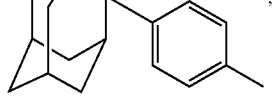
-continued
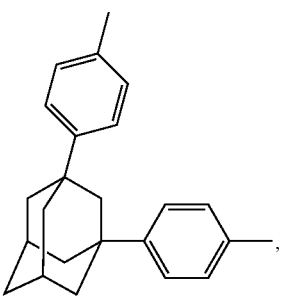
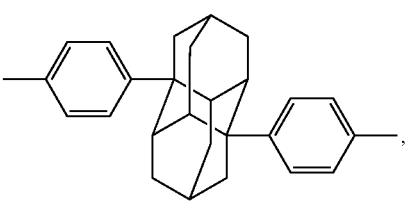
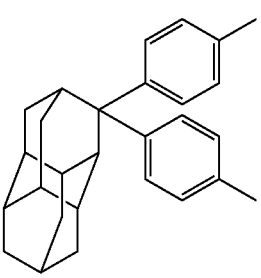
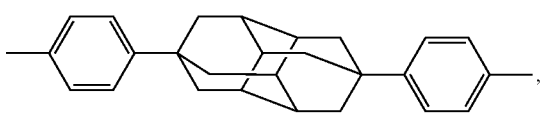
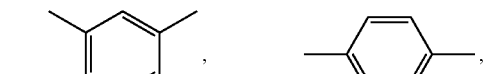
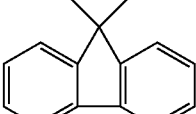
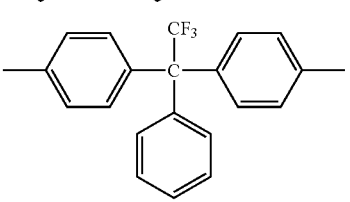

-continued

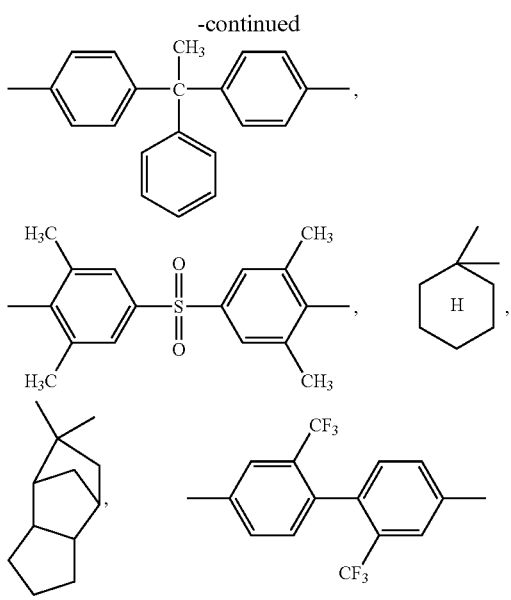

In the method of the present invention, the step is performed at a temperature ranged from 100 to 220° C., an equivalent ratio of the inorganic base and the aromatic diol is less than 3. Furthermore, the 5-halo-2-nitrophenol is one selected from a group consisting of 5-fluoro-2-nitrophenol, 5-chloro-2-nitrophenol, 5-bromo-2-nitrophenol and a combination thereof, the organic solvent is one selected from a group consisting of N,N-dimethylformamide, N,N-dimethylacetamide, dimethyl sulfoxide, 1-methyl-2-pyrrolidone and a combination thereof, and the inorganic base is one selected from a group consisting of a carbonate salt, a hydroxide salt, a fluoride salt and a combination thereof.

EXAMPLE 1

Synthesis of 2,2-Bis(4-(3-hydroxy-4-nitrophenoxy)phenyl)adamantane

A mixture of 2.00 g (6.26 mmol) of 2,2-bis(4-hydroxyphenyl)adamantane, 2.00 g (12.7 mmol) of 5-fluoro-2-nitrophenol, 1.70 g (12.3 mmol) of anhydrous $K_2CO_3$, and 50 mL of dry DMF was reflux for 12 h under nitrogen. The mixture was allowed to cool and subsequently poured into 500 mL of distilled water. The resulting solution was acidied by concentrated hydrogen chloride to pH=3.5~4.0. The precipitated product was collected, washed thoroughly with water until neutral, and then dried to give 2.75 g (73.9%) of 2,2-bis(4-(3-hydroxy-4-nitrophenoxy)phenyl)adamantane. mp 248~250° C.; Elemental Anal. Calcd. for $C_{34}H_{30}N_2O_8$: C, 68.69; H, 5.05; N, 4.71. Found: C, 68.58; H, 5.10; N, 4.68. MS (EI) m/z 594 (M$^+$, 100); IR (KBr): 3402, 2896, 2868, 1576, 1322 cm$^{-1}$.

EXAMPLE 2

Synthesis of 2,2-Bis(4-(4-amino-3-hydroxyphenoxy)phenyl)adamantane

A mixture of 2,2-bis(4-(3-hydroxy-4-nitrophenoxy)phenyl)adamantane (3.00 g, 5.05 mmol), 10% Pd/C (0.06 g) and ethanol (60 mL) were heated to reflux. Then, 20 mL of hydrazine hydrate was added dropwise into the suspension solution over a period of 1 hour. After the mixture was refluxed for another 24 h. The reaction solution was then filtered to remove Pd/C. The crude product was recrystallized from ethanol to give 1.81 g (67.1%) of 2,2-bis(4-(4-amino-3-hydroxyphenoxy)phenyl)adamantane. mp>160° C. (decompose); IR (KBr): 3415, 3298, 2912 cm$^{-1}$, MS (EI) m/z 534 (M$^+$, 100); Anal. Calcd. for $C_{34}H_{34}N_2O_4$: C, 76.40; H, 6.36; N, 5.24. Found: C, 76.21; H, 6.45; N, 5.22.

EXAMPLE 3

Synthesis of 1,3-Bis(4-(3-hydroxy-4-nitrophenoxy)phenyl)adamantane

A mixture of 2.00 g (6.26 mmol) of 1,3-bis(4-hydroxyphenyl)adamantane, 2.00 g (12.7 mmol) of 5-fluoro-2-nitrophenol, 1.70 g (12.3 mmol) of anhydrous $K_2CO_3$, and 50 mL of dry DMF was reflux for 12 h under nitrogen. The mixture was allowed to cool and subsequently poured into 500 mL of distilled water. The resulting solution was acidied by concentrated hydrogen chloride to PH=3.5~4.0. The precipitated product was collected, washed thoroughly with water until neutral, and then dried to give 3.46 g (93.1%) of 1,3-bis(4-(3-hydroxy-4-nitrophenoxy)phenyl)adamantane. mp 118~122° C.; Elemental Anal. Calcd. for $C_{34}H_{30}N_2O_8$: C, 68.69; H, 5.05; N, 4.71. Found: C, 68.56; H, 5.12; N, 4.65. MS (EI) m/z 594 (M$^+$, 100); IR (KBr): 3416, 2890, 2857, 1556, 1342 cm$^{-1}$.

EXAMPLE 4

Synthesis of 1,3-Bis(4-(4-amino-3-hydroxyphenoxy)phenyl)adamantane

A mixture of 1,3-bis(4-(4-amino-3-hydroxyphenoxy)phenyl)adamantane (3.00 g, 5.05 mmol), 10% Pd/C (0.06 g), and ethanol (60 mL) was heated to reflux. Then, 20 mL of hydrazine hydrate was added dropwise into the suspension solution over a period of 1 hour. After the mixture was refluxed for another 24 h. The reaction solution was then filtered to remove Pd/C. The crude product was recrystallized from ethanol to give 1.95 g (72.3%) of 1,3-bis(4-(4-amino-3-hydroxyphenoxy)phenyl)adamantane. mp 166~169° C.; IR (KBr): 3611, 3327, 2920 cm$^{-1}$, MS (EI) m/z 534 (M$^+$, 100); Elemental Anal. Calcd. for $C_{34}H_{34}N_2O_4$: C, 76.40; H, 6.36; N, 5.24. Found: C, 76.32; H, 6.44; N, 5.19.

EXAMPLE 5

Synthesis of 1,3-Bis(3-hydroxy-4-nitrophenoxy)benzene 1,3-Bis(3-hydroxy-4-nitrophenoxy)benzene was synthesized in a manner analogous to Example 1 from resorcinol. Yield: 91.9%; mp 180~182° C.; IR (KBr): 3440, 1615, 1576, 1518, 1465, 1323 cm$^{-1}$; MS (EI) m/z 384 (M$^+$, 100); Elemental Anal. Calcd. for $C_{18}H_{12}N_2O_8$: C, 56.25; H, 3.12; N, 7.29. Found: C, 56.12; H, 3.16; N, 7.24.

EXAMPLE 6

Synthesis of 1,3-Bis(4-amino-3-hydroxyphenoxy)benzene 1,3-Bis(4-amino-3-hydroxyphenoxy)benzene was synthesized in a manner analogous to Example 2 from 1,3-bis (3-hydroxy-4-nitrophenoxy)benzene. Yield: 81%; mp 171~174° C.; IR (KBr): 3414, 3342, 1588, 1518 cm$^{-1}$; MS (EI) m/z 324 (M$^+$, 100); Elemental Anal. Calcd. for $C_{18}H_{16}N_2O_4$: C, 66.67; H, 4.94; N, 8.64. Found: C, 66.45; H, 5.02; N, 8.53.

EXAMPLE 7

Synthesis of 1,4-Bis(3-hydroxy-4-nitrophenoxy)benzene 1,4-Bis(3-hydroxy-4-nitrophenoxy)benzene was synthesized in a manner analogous to Example 1 from hydroquinone. Yield: 90%; mp 242~245° C.; IR (KBr): 3435, 1591, 1531, 1368, 1321 cm$^{-1}$; MS (EI) m/z 384 (M$^+$, 100); Elemental Anal. Calcd. for $C_{18}H_{12}N_2O_8$: C, 56.25; H, 3.12; N, 7.29. Found: C, 56.15; H, 3.18; N, 7.21.

EXAMPLE 8

Synthesis of 1,4-Bis(4-amino-3-hydroxyphenoxy)benzene 1,4-Bis(4-amino-3-hydroxyphenoxy)benzene was synthesized in a manner analogous to Example 2 from 1,4-bis(3-hydroxy-4-nitrophenoxy)benzene. Yield: 83%; mp>220° C. (decompose); IR (KBr): 3360, 3288, 3040, 1603, 1514 cm$^{-1}$; MS (EI) m/z 324 (M$^+$, 100); Elemental Anal. Calcd. for $C_{18}H_{16}N_2O_4$: C, 66.67; H, 4.94; N, 8.64. Found: C, 66.52; H, 5.01; N, 8.56.

EXAMPLE 9

Synthesis of 1,2-Bis(3-hydroxy-4-nitrophenoxy)benzene 1,2-Bis(3-hydroxy-4-nitrophenoxy)benzene was synthesized in a manner analogous to Example 1 from catechol. Yield: 90.2%; mp 178~180° C.; IR (KBr): 3420, 1585, 1510, 1325 cm$^{-1}$; MS (EI) m/z 384 (M$^+$, 100); Elemental Anal. Calcd. for $C_{18}H_{12}N_2O_8$: C, 56.25; H, 3.12; N, 7.29. Found: C, 56.11; H, 3.21; N, 7.23.

EXAMPLE 10

Synthesis of 1,2-Bis(4-amino-3-hydroxyphenoxy)benzene 1,2-Bis(4-amino-3-hydroxyphenoxy)benzene was synthesized in a manner analogous to Example 2 from 1,2-bis(3-hydroxy-4-nitrophenoxy)benzene. Yield: 75.1%; mp>180° C. (decompose); IR (KBr): 3362, 3295, 3035, 1601 cm$^{-1}$; MS (EI) m/z 324 (M$^+$, 100); Elemental Anal. Calcd. for $C_{18}H_{16}N_2O_4$: C, 66.67; H, 4.94; N, 8.64. Found: C, 66.28; H, 5.04; N, 8.52.

EXAMPLE 11

Synthesis of 1,4-Bis(3-hydroxy-4-nitrophenoxy)-2-tert-butyl benzene 1,4-Bis(3-hydroxy-4-nitrophenoxy)-2-tert-butyl benzene was synthesized in a manner analogous to Example 1 from tert-butyl hydroquindne. Yield: 91.5%; mp 156~158° C.; IR (KBr): 3430, 1611, 1589, 1524, 1465, 1322 cm$^{-1}$; MS (EI) m/z 440 (M$^+$, 100); Elemental Anal. Calcd. for $C_{22}H_{20}N_2O_8$: C, 60.00; H, 4.55; N, 6.36. Found: C, 59.82; H, 4.62; N, 6.23.

EXAMPLE 12

Synthesis of 1,4-Bis(4-amino-3-hydroxy phenoxy)-2-tert-butyl benzene 1,4-Bis(4-amino-3-hydroxyphenoxy)-2-tert-butyl benzene was synthesized in a manner analogous to Example 2 from 1,4-bis(3-hydroxy-4-nitrophenoxy)-2-tert-butyl benzene. Yield: 80.2%; mp 110~113° C.; IR (KBr): 3400, 3360, 3210, 1576, 1499 cm$^{-1}$; MS (EI) m/z 380 (M$^+$, 100); Elemental Anal. Calcd. for $C_{22}H_{24}N_2O_4$: C, 69.47; H, 6.32; N, 7.37. Found: C, 69.24; H, 6.43; N, 7.31.

EXAMPLE 13

Synthesis of Bis(4-(3-hydroxy-4-nitrophenoxy)phenyl)sulfone

Bis(4-(3-hydroxy-4-nitrophenoxy)phenyl)sulfone was synthesized in a manner analogous to Example 1 from 4,4-sulfonyldiphenol. Yield: 87.2%; mp 220~222° C.; IR (KBr): 3402, 1614, 1574, 1521, 1496, 1321 cm$^{-1}$; MS (EI) m/z 524 (M$^+$, 100); Elemental Anal. Calcd. for $C_{24}H_{16}N_2O_{10}S$: C, 54.96; H, 3.05; N, 5.34. Found: C, 54.72; H, 3.13; N, 5.26.

EXAMPLE 14

Synthesis of Bis(4-(4-amino-3-hydroxyphenoxy)phenyl)sulfone

Bis(4-(4-amino-3-hydroxyphenoxy)phenyl)sulfone was synthesized in a manner analogous to Example 2 from bis(4-(3-hydroxy-4-nitrophenoxy)phenyl)sulfone. Yield: 83.5%; mp 228~231° C.; IR (KBr): 3318, 1577, 1511 cm$^{-1}$; MS (EI) m/z 464 (M$^+$, 100); Elemental Anal. Calcd. for $C_{24}H_{20}N_2O_6S$: C, 62.07; H, 4.31; N, 6.03. Found: C, 61.83; H, 4.39; N, 5.96.

EXAMPLE 15

Synthesis of 2,2-Bis(4-(3-hydroxy-4-nitrophenoxy)phenyl)hexafluoropropane 2,2-Bis(4-(3-hydroxy-4-nitrophenoxy)phenyl)hexafluoropropane was synthesized in a manner analogous to Example 1 from 2,2-bis(4-hydroxyphenyl)hexafluoropropane. Yield: 83.2%; mp 148~151° C.; IR (KBr): 3410, 1631, 1565, 1531, 1325, 1321 cm$^{-1}$; MS (EI) m/z 610 (M$^+$, 100); Elemental Anal. Calcd. for $C_{27}H_{16}F_6N_2O_8$: C, 53.11; H, 2.62; N, 4.59. Found: C, 52.96; H, 2.68; N, 4.51.

EXAMPLE 16

Synthesis of 2,2-Bis(4-(4-amino-3-hydroxyphenoxy)phenyl)hexafluoropropane 2,2-Bis(4-(4-amino-3-hydroxyphenoxy)phenyl)hexafluoropropane was synthesized in a manner analogous to Example 2 from 2,2-bis(4-(3-hydroxy-4-nitrophenoxy)phenyl)hexafluoropropane. Yield: 81.7%; mp 178~181° C.; IR (KBr): 3380, 3250, 1599, 1500 cm$^{-1}$; MS (EI) m/z 550 (M$^+$, 100); Elemental Anal. Calcd. for $C_{27}H_{20}F_6N_2O_4$: C, 58.91; H, 3.64; N, 5.09. Found: C, 58.73; H, 3.72; N, 5.00.

EXAMPLE 17

Synthesis of 2,3-Bis(3-hydroxy-4-nitrophenoxy)naphthalene 2,3-Bis(3-hydroxy-4-nitrophenoxy)naphthalene was synthesized in a manner analogous to Example 1 from 2,3-dihydroxynaphthalene. Yield: 89.2%, mp 179~181° C.; IR (KBr): 3410, 3100, 1615, 1580, 1323 cm$^{-1}$; MS (EI) m/z 434 (M$^+$, 100); Elemental Anal. Calcd. for $C_{22}H_{14}N_2O_8$: C, 60.83; H, 3.23; N, 6.45. Found: C, 60.78; H, 3.25; N, 6.43.

EXAMPLE 18

Synthesis of 2,3-Bis(4-amino-3-hydroxyphenoxy)naphthalene 2,3-Bis(4-amino-3-hydroxyphenoxy)naphthalene was synthesized in a manner analogous to Example 2 from 2,3-bis(3-hydroxy-4-nitrophenoxy)naphthalene. Yield: 82.4%; mp 196~197° C., IR (KBr) 3292, 3352, 1497 cm$^{-1}$; MS (EI) m/z 374 (M$^+$, 100); Elemental Anal. Calcd. for $C_{22}H_{18}N_2O_4$: C, 70.59; H, 4.81; N, 7.49. Found: C, 70.38; H, 4.87; N, 7.43.

EXAMPLE 19

Synthesis of 2,7-Bis(3-hydroxy-4-nitrophenoxy)naphthalene 2,7-Bis(3-hydroxy-4-nitrophenoxy)naphthalene was synthesized in an analogous Example 1 from 2,7-dihydorxynaphthalene. Yield 87.2%; mp 218~220° C.; IR (KBr): 3408, 3095, 1612, 1575, 1325 cm$^{-1}$; MS (EI) m/z 434 (M$^+$, 100); Elemental Anal. Calcd. for $C_{22}H_{14}N_2O_8$: C, 60.83; H, 3.23; N, 6.45. Found: C, 60.80; H, 3.23; N, 6.42.

EXAMPLE 20

Synthesis of 2,7-Bis(4-amino-3-hydroxyphenoxy)naphthalene 2,7-Bis(4-amino-3-hydroxyphenoxy)naphthalene was synthesized in a manner analogous to Example 2 from 2,7-bis(3-hydroxy-4-nitrophenoxy)naphthalene. Yield: 78.6%; mp 201~210° C.; IR (KBr) 3295, 3362, 1495 cm$^{-1}$; MS (EI) m/z 374 (M$^+$, 100); Elemental Anal. Calcd. for $C_{22}H_{18}N_2O_4$: C, 70.59; H, 4.81; N, 7.49. Found: C, 70.42; H, 4.88; N, 7.42.

EXAMPLE 21

Synthesis of 1,5-Bis(3-hydroxy-4-nitrophenoxy)naphthalene 1,5-Bis(3-hydroxy-4-nitrophenoxy)naphthalene was synthesized in a manner analogous to Example 1 from 1,5-dihydroxynaphthalene. Yield: 85.7% mp 238~241° C.; IR (KBr): 3405, 3102, 1612, 1578, 1328 cm$^{-1}$; MS (EI) m/z 434 (M$^+$, 100); Elemental Anal. Calcd. for $C_{22}H_{14}N_2O_8$: C, 60.83; H, 3.23; N, 6.45. Found: C, 60.79; H, 3.27; N, 6.41.

EXAMPLE 22

Synthesis of 1,5-Bis(4-amino-3-hydroxyphenoxy)naphthalene 1,5-Bis(4-amino-3-hydroxyphenoxy)naphthalene was synthesized in a manner analogous to Example 2 from 1,5-bis(3-hydroxy-4-nitrophenoxy)naphthalene. Yield: 78.9%; mp 251~253° C., IR (KBr) 3292, 3365, 1498 cm$^{-1}$; MS (EI) m/z 374 (M$^+$, 100); Elemental Anal. Calcd. for $C_{22}H_{18}N_2O_4$: C, 70.59; H, 4.81; N, 7.49. Found: C, 70.48; H, 4.88; N, 7.46.

EXAMPLE 23

Synthesis of 2,6-Bis(3-hydroxy-4-nitrophenoxy)naphthalene 2,6-Bis(3-hydroxy-4-nitrophenoxy)naphthalene was synthesized in a manner analogous to Example 1 from 2,6-dihydroxynaphthalene. Yield 89.6%; mp 244~246° C.; IR (KBr): 3409, 3095, 1610, 1575, 1325 cm$^{-1}$; MS (EI) m/z 434 (M$^+$, 100); Elemental Anal. Calcd. for $C_{22}H_{14}N_2O_8$: C, 60.83; H, 3.23; N, 6.45. Found: C, 60.78; H, 3.28; N, 6.42.

EXAMPLE 24

Synthesis of 2,6-Bis(4-amino-3-hydroxyphenoxy)naphthalene 2,6-Bis(4-amino-3-hydroxyphenoxy)naphthalene was synthesized in a manner analogous to Example 2 from 2,6-bis(3-hydroxy-4-nitrophenoxy)naphthalene. Yield 85.0%; mp 239~241° C.; IR (KBr) 3295, 3367, 1499 cm$^{-1}$; MS (EI) m/z 374 (M$^+$, 100); Elemental Anal. Calcd. for $C_{22}H_{18}N_2O_4$: C, 70.59; H, 4.81; N, 7.49. Found: C, 70.51; H, 4.86; N, 7.462.

The present invention provides a method for preparing a bis(o-nitrophenol) compound of the formula (I). Certainly, the bis(o-nitrophenol) compound of the formula (I) was further hydrogenated to obtain the corresponding bis(o-aminophenol)(II). The bis(o-aminophenols) is particularly useful as curing agents for epoxy resins and as monomers in the preparation of polybenzoxazoles. The present invention further provides a pharmaceutical composition for inhibiting a growth of tumor cells, wherein the pharmaceutical. composition includes the bis(o-aminophenols) prepared by the present invention.

In vitro and in vivo growth inhibition and G1 arrest in human cancer cells by diaminophenyladamantane derivatives disclosed by the inventor and published on p697-705 Vol. 15 No. 7, Anti-Cancer Drugs, 2004 is incorporated as a reference hereafter.

In Vitro Anticancer Activity of 1,3-substituted diaminophenyladamantane derivatives Comparison of anticancer activities of the 1,3-substituted adamantane derivatives, 1,3-bis(4-aminophenyl)adamantane (1,3-DPANH$_2$), 1,3-bis(4-(aminophenoxy)phenyl)adamantane (1,3-DPAONH$_2$), 1,3-bis(4-(4-amino-3-hydroxy)phenyl)adamantane (1,3-DPA/OH/NH$_2$) and 1,3-bis(4-(4-amino-2-trifluoromethylphenoxy)phenyl)adamantane (1,3-DPA/CF$_3$/NH$_2$) as shown in FIG. 1 were synthesized in the present invention. Those compounds were submitted to the National Cancer Institute for anticancer assay in culture against a standard panel of cell lines. The results of growth inhibition assays using a number of lines of different tissue origin are given in Table 1. The IC$_{50}$ of 1,3-DPANH$_2$ and 1,3-DPAONH$_2$ were found to be <10 μM against 3(6%) and 32(60%) cell lines, respectively. Comparison of anticancer activities of 1,3-DPANH$_2$ and 1,3-DPAONH$_2$ indicated that 1,3-DPAONH$_2$ exhibited stronger growth inhibitory on anticancer activities than 1,3-DPANH$_2$. The results suggest that the configuration of 1,3-DPAONH$_2$ plays a prominent role in their anticancer activities. To further confirm that the different substituents (CF$_3$ and OH) on the phenyl ring of 1,3-DPAONH$_2$ affect the growth inhibition of cancer cells. The IC$_{50}$ of 1,3-DPA/CF$_3$/NH$_2$ and 1,3-DPA/OHiNH$_2$ were found to be <5 μM against 0(0%) and 47(89%) cell lines, respectively, suggesting that the OH group was favorable for anticancer activities whereas the CF$_3$ group was unfavorable. The transformations of 1,3-DPAONH$_2$ to 1,3-DPA/OH/NH$_2$ led to a remarked enhancement of anticancer activity toward all the tested cancer lines. The role of the OH group at the ortho position of the NH$_2$ on growth inhibition is remarkable. In addition, one compound (1,3-DPA/OH/NH$_2$) was confirmed to have an IC$_{50}$ of <1 μM against one of the cells (BT-549 breast carcinoma). Comparison of anticancer activities of 1,3-substituted diaminophenyladamantane derivatives, the following order of potency against the tested cancer lines was observed: 1,3-DPA/OH/NH$_2$>1,3-DPAONH$_2$>1,3-DPANH$_2$>1,3-DPA/CF$_3$/NH$_2$.

TABLE 1

In vitro anticancer activity of 1,3-substituted diaminophenyladamantane (NCI panel)

| cell line | IC$_{50}$ (μM)[a] | | | |
|---|---|---|---|---|
| | DPANH$_2$ | DPAONH$_2$ | DPA/OH/NH$_2$ | DPA/CF$_3$/NH$_2$ |
| Leukemia | | | | |
| CCRF-CEM | 15.7 | 4.83 | b | 36.2 |
| HL-60(TB) | 30.9 | 17.1 | 2.12 | 24.2 |
| K-562 | 14.6 | 7.08 | 3.46 | 43.9 |
| MOLT-4 | 11.3 | 3.81 | 2.42 | 35.7 |
| RPMI-8226 | 10.7 | 4.14 | 2.54 | b |
| NSCLS | | | | |
| A549/ATCC | >100 | 10.3 | 1.52 | 19.0 |
| EKVX | 36.6 | 15.6 | 1.68 | 15.4 |
| HOP-62 | 60 | 10.7 | 5.53 | 18.2 |
| NCI-H226 | 11.5 | 23.2 | 5.05 | 19.4 |
| NCI-H23 | 59.6 | 6.92 | 1.86 | 17.7 |
| NCI-H322M | b | 8.84 | 1.26 | 20.1 |
| NCI-H522 | b | 13.3 | 1.40 | 14.4 |
| Colon cancer | | | | |
| COLO 205 | 2.30 | 13.3 | 1.84 | 19.1 |
| HCT-116 | 44.3 | 5.65 | 1.39 | 24.9 |
| HCT-15 | 14.5 | 4.99 | 1.76 | 31.8 |
| HT29 | b | 7.12 | b | 17.2 |
| KM12 | >100 | 4.07 | 1.72 | 21.0 |
| SW-620 | 3.14 | 6.52 | 2.89 | 36.3 |
| CNS cancer | | | | |
| SF-268 | 45.2 | 5.60 | 1.16 | 17.4 |
| SF-295 | 16.4 | 6.91 | 2.29 | 25.3 |
| SNB-19 | 37.8 | 8.66 | 1.31 | 22.5 |
| U251 | 14.3 | 7.90 | 1.30 | 14.5 |
| Melanoma | | | | |
| LOX IMVI | >100 | 2.44 | 1.64 | 17.9 |
| MALME-3M | b | 14.6 | 1.93 | 22.2 |
| M14 | 37.1 | 9.62 | 1.59 | 16.9 |
| SK-MEL-2 | 35.9 | 15.7 | 2.45 | 14.1 |
| SK-MEL-28 | 15 | 18.8 | 2.74 | 43.2 |
| SK-MEL-5 | 13.1 | 13.8 | 1.88 | 22.0 |
| UACC-257 | 75.5 | 12.5 | 2.23 | 18.7 |
| UACC-62 | 29 | 9.64 | 2.65 | 22.1 |
| Ovarian cancer | | | | |
| IGROV1 | >100 | 2.64 | 1.38 | 19.5 |
| OVCAR-3 | 48.5 | 3.08 | 1.85 | 17.9 |
| OVCAR-4 | 10.2 | 6.98 | 2.02 | 36.6 |
| OVCAR-5 | 27.6 | 19.1 | b | 27.0 |
| OVCAR-8 | 85.1 | 4.82 | 2.03 | 16.0 |
| Renal cancer | | | | |
| 786-0 | 38.5 | 8.09 | 2.83 | 31.5 |
| A498 | 15.7 | 18.0 | 4.54 | 18.3 |
| ACHN | 41.1 | 11.7 | 1.61 | 32.9 |
| CAKI-1 | >100 | 12.1 | 1.82 | 28.1 |
| RXF-393 | b | 7.78 | 1.61 | 11.1 |
| SN12C | 25.1 | 5.76 | 1.74 | 31.1 |
| TK-10 | >100 | 24.9 | 5.57 | 16.1 |
| UO-31 | 4.87 | 13.6 | 1.95 | 39.1 |
| Prostate cancer | | | | |
| PC-3 | b | 11.5 | 1.94 | 14.8 |
| DU-145 | 51.2 | 6.41 | 1.72 | 35.2 |
| Breast cancer | | | | |
| MCF-7 | 31.9 | 2.89 | 1.85 | 13.4 |
| NCI/ADR-RES | 56.8 | 8.59 | 2.32 | 21.7 |
| MDA-MB-231 | 19.6 | 16.9 | 1.62 | 15.2 |
| HS 578T | b | 11.7 | 1.63 | 17.1 |
| MDA-MB-435 | b | 5.22 | 1.92 | 24.2 |
| MDA-N | 37.7 | 4.33 | 1.58 | 36.7 |
| BT-549 | 42.8 | 4.02 | 0.565 | 21.9 |
| T-47D | b | 5.67 | 1.66 | 15.1 |

[a] Cells in RPMI 1640 medium containing 2 mM L-glutamine and 5% fetal bovine serum (heat-inactivated) were exposed to drug for the last 48 h of a 72 h incubation at 37° C. in a 5% CO$_2$ humidified atmosphere and then stained for total protein with sulforhodamine B as described (J Natl. Cancer Inst. 1991; 93; 757-66).
b Not determined.

In Vitro Anticancer Activity of 2,2-substituted diaminophenyladamantane derivatives Comparison of anticancer activities of the 2,2-substituted adamantane derivatives, 2,2-bis(4-aminophenyl)adamantane (2,2-DPANH$_2$), 2,2-bis(4-(4-aminophenoxy)phenyl)adamantane (2,2-DPAONH$_2$) and 2,2-bis(4-(4-amino-3-hydroxyphenoxy)phenyl)adamantane (DPA) as shown in FIG. 1 were synthesized in the present invention. The results of growth inhibition of those compounds in vitro against NCI's human cancer cell lines are given in Table 2. The IC$_{50}$ of 2,2-DPANH$_2$ and 2,2-DPAONH$_2$ were found to be <10 μM against 9(17%) and 40(75%) cell lines, respectively. Comparison of anticancer activities of 2,2-DPANH$_2$ and 2,2-DPAONH$_2$ indicated that 2,2-DPAONH$_2$ exhibited stronger growth inhibitory on anticancer activities than 2,2-DPANH$_2$. In addition, the transformations of 2,2-DPAONH$_2$ to DPA led to a remarked enhancement of anticancer activity toward all the tested cancer lines. The role of the OH group at the ortho position of the NH$_2$ on growth inhibition is remarkable. The IC$_{50}$ of DPA was found to be <3 μM against 48(91%) cell lines. Interestingly, one compound (2,2-DPANH$_2$) was found to have an IC$_{50}$<0.1 μM against three of the cells (KM 12 colon, SF-295 CNS, NCI/ADR-RES breast carcinoma). Comparison of anticancer activities of 2,2-substituted diaminophenyladamantane derivatives, the following order of potency against the tested cancer lines was observed: DPA>2,2-DPAONH$_2$>2,2-DPANH$_2$. Referring to Table 1 and Table 2, comparison of anticancer activities of 1,3- and 2,2-substituted diaminophenyladamantane derivatives indicated that 2,2-substituted adamantane derivatives exhibited stronger growth inhibitory on anticancer activities than the corresponding 1,3-substituted analogues. We noted that 1,3-DPA/OH/NH$_2$ and DPA exhibited strong growth inhibitory activities in vitro against the tested cancer cell lines.

TABLE 2

In vitro anticancer activity of 2,2-substituted diaminophenyladamantane (NCI panel)

| cell line | IC$_{50}$ (μM)$^a$ | | |
|---|---|---|---|
| | DPANH$_2$ | DPAONH$_2$ | DPA |
| Leukemia | | | |
| CCRF-CEM | 3.76 | 3.03 | 3.08 |
| HL-60(TB) | 19.2 | 5.00 | 2.05 |
| K-562 | 10.3 | 3.89 | 1.98 |
| MOLT-4 | 4.96 | 4.27 | 1.45 |
| RPMI-8226 | b | 3.01 | 1.92 |
| NSCLC | | | |
| A549/ATCC | b | 3.38 | 1.94 |
| EKVX | 16.4 | 4.76 | 2.63 |
| HOP-62 | 13.6 | 11.8 | 2.11 |
| NCI-H226 | 12.4 | 21.4 | 1.94 |
| NCI-H23 | 19.9 | 5.15 | 1.84 |
| NCI-H322M | b | 0.184 | 1.41 |
| NCI-H522 | 15.6 | 4.28 | 1.60 |
| Colon cancer | | | |
| COLO 205 | b | 2.71 | 0.484 |
| HCT-116 | 20.9 | 2.71 | 1.58 |
| HCT-15 | 21.9 | 4.94 | 1.67 |
| HT29 | 0.1 | 2.96 | 1.81 |
| KM12 | 0.01 | 3.55 | 2.02 |
| SW-620 | 11.4 | 5.03 | 1.63 |
| CNS cancer | | | |
| SF-268 | 1.57 | 6.44 | 1.62 |
| SF-295 | 0.059 | 6.76 | 2.57 |
| SNB-19 | 14.6 | 10.1 | 3.01 |
| U251 | 18.6 | 2.81 | 1.70 |
| Melanoma | | | |
| LOX IMVI | 16.2 | 2.75 | 1.69 |
| MALME-3M | b | 13.6 | 2.02 |
| M14 | 14.9 | 2.28 | 1.69 |
| SK-MEL-2 | 18.5 | 16.8 | 1.69 |
| SK-MEL-28 | 14.9 | 10.5 | 1.68 |
| SK-MEL-5 | b | 8.38 | 1.56 |
| UACC-257 | 19.2 | 5.76 | 2.32 |
| UACC-62 | 16.3 | 17.7 | 3.21 |
| Ovarian cancer | | | |
| IGROV1 | 9.6 | 5.88 | 1.75 |
| OVCAR-3 | 10.9 | 2.58 | 1.56 |
| OVCAR-4 | 14.3 | 6.96 | 3.07 |
| OVCAR-5 | 15.8 | 15.3 | 2.08 |
| OVCAR-8 | 7.73 | 5.82 | 1.68 |
| Renal cancer | | | |
| 786-0 | b | 3.07 | 1.88 |
| A498 | 21 | 2.91 | 4.67 |
| ACHN | 18.6 | 13.4 | 1.78 |
| CAKI-1 | 15 | 11.1 | 2.32 |
| RXF-393 | 2.74 | b | 1.82 |
| SN12C | 18.6 | 3.65 | 1.83 |

TABLE 2-continued

In vitro anticancer activity of 2,2-substituted diaminophenyladamantane (NCI panel)

| cell line | IC$_{50}$ (μM)$^a$ | | |
|---|---|---|---|
| | DPANH$_2$ | DPAONH$_2$ | DPA |
| TK-10 | 18 | 14.3 | 2.16 |
| UO-31 | 18.3 | 3.02 | 1.85 |
| Prostate cancer | | | |
| PC-3 | 14.9 | 6.75 | 1.60 |
| DU-145 | b | 3.31 | 2.06 |
| Breast cancer | | | |
| MCF-7 | 19.4 | 3.81 | 1.93 |
| NCI/ADR-RES | 0.079 | 15.8 | 2.33 |
| MDA-MB-231 | 17.4 | 17.0 | 1.82 |
| HS 578T | b | 4.91 | 2.35 |
| MDA-MB-435 | 14.7 | 6.04 | 2.30 |
| MDA-N | 18.6 | 2.74 | 2.14 |
| BT-549 | 11.2 | 4.28 | 2.05 |
| T-47D | 14.4 | b | 4.13 |

$^a$Cell in RPMI 1640 medium containing 2 mM L-glutamine and 5% fetal bovine serum (heat-inactivated) were exposed to drug for the last 48 h of a 72 h incubation at 37° C. in a 5% CO$_2$ humidified atmosphere and then stained for total protein with sulforhodamine B as described (J Natl. Cancer Inst. 1991; 93; 757-66).
b Not determined.

Cell Cycle Analysis

The cell cycle progression of Colo205, HT 29 and HCT-15 cells was examined using flow cytometry after exposure to 1, 2, 4 or 8 μM DPA for 72 hours. Table 3 shows that majority of Colo 205 cells accumulated in G$_1$ phase (84.1-87.1%) with a decrease of cells in S phase (7.8-10.3%) and G$_2$/M phase (5.1-5.6%) after treatment with 2 μM DPA for 48-72 h. HT-29 cells were mainly in G$_0$/G$_1$ phase (84.1-86.0%), and only a few percent of cells in S phase (7.4-8.0%) after exposure to 4 μM DPA for 48-72 h. The obviously decreased G$_2$/M phase (6.9-7.6%) of HCT-15 cell populations was observed after their exposure to 8 μM DPA for 24-48 h. The G$_0$/G$_1$ arrest was not induced in the HCT-15 cells treated with 1-8 μM DPA for 24-72 h. These results showed that the cell cycle progression in DPA-treated cell lines was heterogeneous. Treatment of Colo 205 and HT-29 cells with DPA resulted in increased G$_0$/G$_1$ phase with concomitant decrease of cells in S phase. DPA exerted the dose specific effect for the induced G$_0$/G$_1$ arrest on Colo 205 cells. The multidrug-resistant HCT-15 showed different pattern of cell cycle histogram from the Colo 205 and HT 29 after DPA treatment. In addition, we noted that DPA-mediated accumulation of Colo205 and HT 29 cells in G$_1$ phase (>80%) was similar to that of DPD (*Anti-Cancer Drug* 2004; 15:277-80). It is likely that the induced G$_1$-arrest without concomitant apoptosis on Colo 205 and HT 29 colon cancer cells is one unique property of structure I.

Structure I

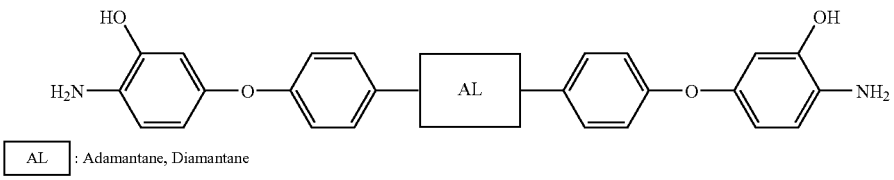

AL: Adamantane, Diamantane $G_1$ phase of the cell cycle is an important period, where various signals interact to determine the proliferation, quiescence, differentiation or apoptosis of cells. Interestingly, DPA exerted $G_0/G_1$ cell-cycle arrest, but not obvious apoptotic inducing activities in human colon cancer cells lines. Thus, we infer that the induced differentiation of DPA-treated colon cancer cells is possible. The differentiation inducing effect of DPA on colon cancer cells will be further examined.

The Irreversible Effect of DPA-Induced Growth Inhibition of Colo 205

Figure 2B:
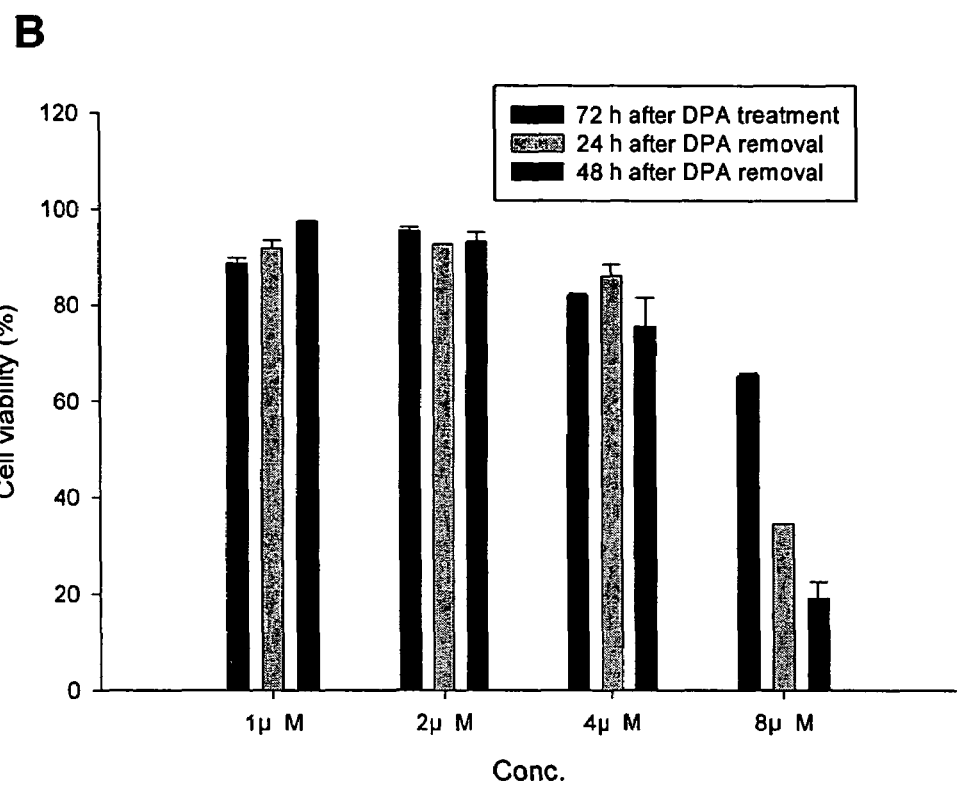
FIG. 2B is a chart showing the cell's viability was examined by haemocytometer.

To further investigate whether the DPA-induced growth inhibition was reversible, Colo 205 cells were treated with DPA for 72 hours, and the cells were withdrawn from DPA by culturing in fresh medium for another 48 or 72 hours. As shown in FIG. 2A at 48-72 hours after removal of 1 μM DPA from the medium the proliferation activity of Colo 205 was reversed and returned to control level. However, no reversal effect was observed after 2, 4 or 8 μM DPA treatment. The viabilities of treated or non-treated cells were >90%, except the cells after 8 μM DPA treatment as shown in FIG. 2B. These results showed DPA could induce irreversible antiproliferation effect on Colo 205 cells, and this property was also similar to that of DPD (*Anti-cancer Drug* 2004; 15: 277-86). These results highlight the important properties of irreversible anticancer activity of adamantane and diamantane derivatives. One possibility is that the relatively lipophilic nature of DPA or DPD reduced cellular efflux after the initial drug exposure. It is inferred that the irreversible property of adamantane and diamantane derivatives provides an advantage to prolong the anticancer activity.

In Vivo Antiproliferation Effect of DPA for Human Colon Cancer Xenografts

Figure 3A:
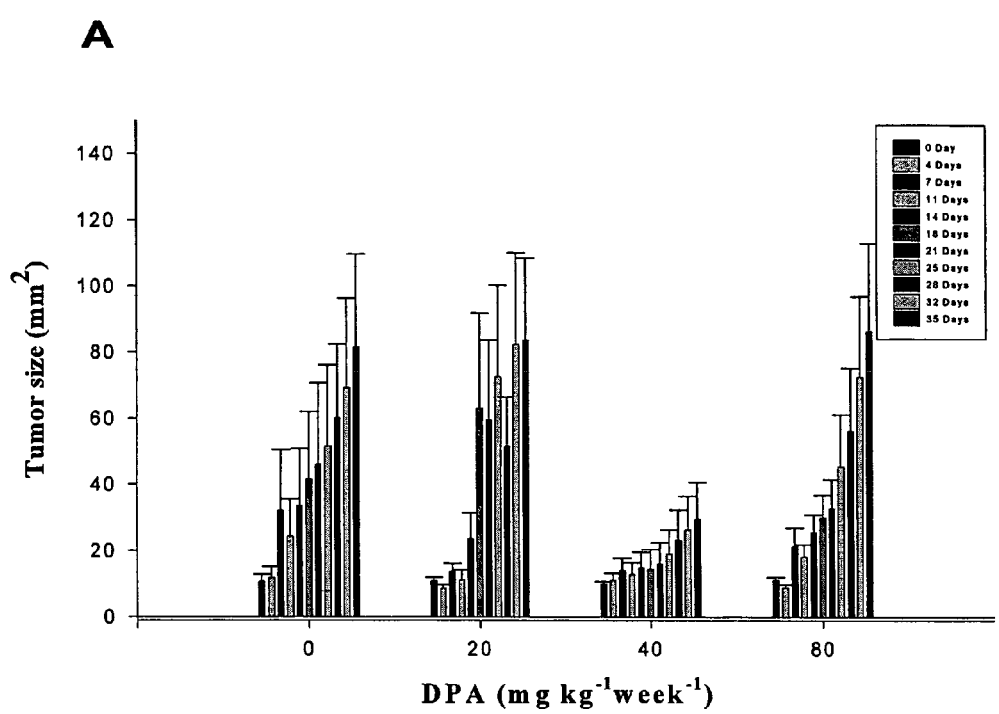
FIG. 3A is a chart showing the in vivo antiproliferation effect of DPA for human colon cancer Colo 205 xenografts.

We further examined whether DPA is also effective in vivo after tumor formation. For compare the in vivo antitumor activity with DPD (DPA analogue), we followed the method of our previous study (*Br. J Cancer* 2003; 89: 1995-2003), and the similar doses were used. Cancer cells were transplanted into ICR nude mice, and when the tumors were palpable (2-4 mm), the mice were treated either with vehicle control or DPA (20-80 mg kg$^{-1}$, i.p., once a week). Treatment of nude mice with DPA (40 mg kg$^{-1}$), the tumor size (mm$^2$) was significantly (P<0.05) decreased in mice as compared to control groups. As shown in FIG. 3A, the tumor size from control animals showed an average of 81.5 mm$^2$ at the end of this study. In contrast, the tumor size from DPA (40 mg kg$^{-1}$)-treated animals had an average of only 29.6 mm$^2$. The tumor size of DPA-treated animals (20 mg kg$^{-1}$ and 80 mg kg$^{-1}$) was not significantly decreased compared to the vehicle control at the end point. While treatment of the in vivo Colo 205 model at 40 mg kg$^{-1}$ led to an apparent decrease in tumor size, exposure to 80 mg kg$^{-1}$ apparently did not as shown in FIG. 3A. The result might be explained by the two possible causes: (i) One mouse had an abnormally large tumor size among the DPA 80 mg Kg$^{-1}$-treated mice. Its tumor size (48.6 mm$^2$) was about 3-fold larger than the average tumor size (16.7 mm$^2$) of the other DPA 80 mg kg$^{-1}$-treated mice at 7 days after the initial treatment. This result may be due to the idiopathic property of the mouse. (ii) DPA presented the dose-specific effect for antitumor activity on human colon cancer xenografts. The dose-specific phenomenon was also found in vitro study of DPA-induced cell cycle arrest on Colo 205 cells as shown in Table 3.

Figure 3B:
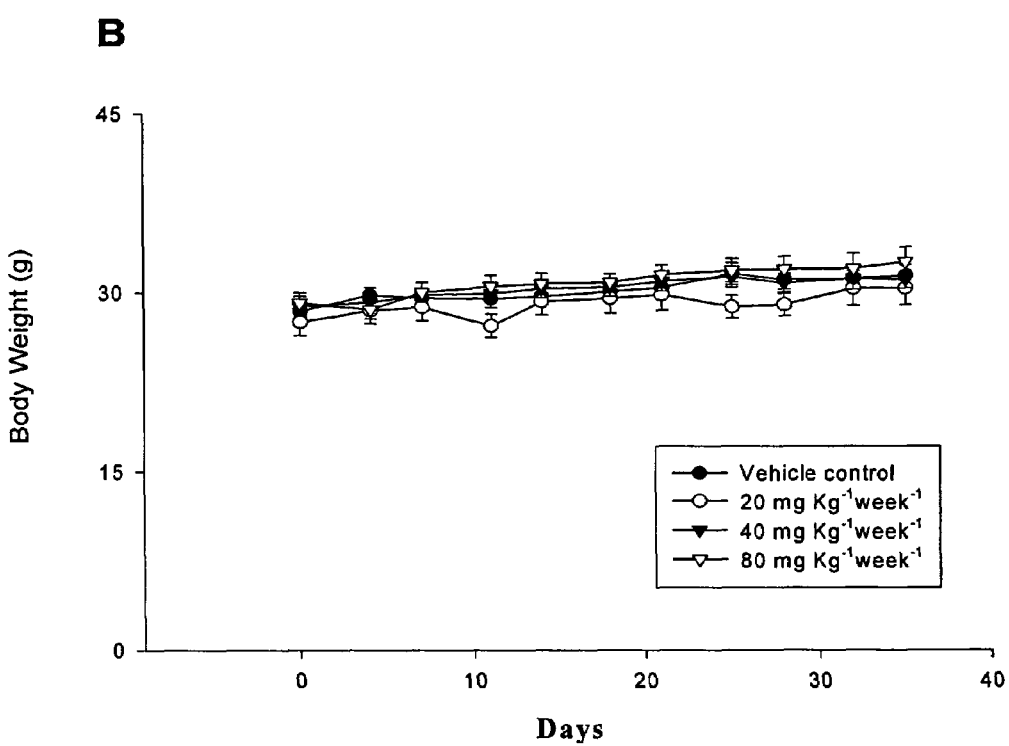
FIG. 3B is a chart showing the changes in body weight of nude mice after treatment with DPA.

It is suggested that the concentration of maximum effect of DPA-induced in vivo antitumor effect is about 40 mg kg$^{-1}$ week$^{-1}$ and this effective dose is similar to DPD (*Br. J Cancer* 2003; 89:1995-2003). The challenge of DPA (20-80 mg kg$^{-1}$, i.p., once a week) in nude mice throughout the experiment produced no obviously acute toxicity. No significant reduction in body weight was found in DPA-treated mice as shown in FIG. 3B. These results show the less toxic property of DPA.

TABLE 3

The effect of DPA on cell cycle progression in three colon cancer cell lines[a]

| | | Colo 205 | | | HT-29 | | | HCT-15 | | |
|---|---|---|---|---|---|---|---|---|---|---|
| | | G0/G1(%) | S(%) | G2/M(%) | G0/G1(%) | S(%) | G2/M(%) | G0/G1(%) | S(%) | G2/M(%) |
| 24 h | Control | 53.7[b] | 33.1 | 13.2 | 50.8 | 38.8 | 10.5 | 36.8 | 44.1 | 19.0 |
| | 1 μM | 58.9 | 29.0 | 12.0 | 56.6 | 33.1 | 10.3 | 31.4 | 50.6 | 18.1 |
| | 2 μM | 67.1 | 24.1 | 48.3 | 67.0 | 23.1 | 10.0 | 31.8 | 54.0 | 14.2 |
| | 4 μM | 67.5 | 24.3 | 8.2 | 72.1 | 17.1 | 10.9 | 30.6 | 58.2 | 11.2 |
| | 8 μM | 70.5 | 24.3 | 5.2 | 77.0 | 13.3 | 9.6 | 39.6 | 53.5 | 6.9 |
| 48 h | Control | 54.8 | 35.9 | 9.3 | 59.3 | 31.5 | 9.3 | 43.9 | 40.3 | 15.8 |
| | 1 μM | 53.3 | 39.0 | 7.6 | 61.6 | 29.0 | 9.4 | 39.1 | 45.1 | 15.8 |
| | 2 μM | 84.1 | 10.3 | 5.6 | 77.5 | 17.8 | 4.7 | 35.2 | 48.8 | 16.0 |

TABLE 3-continued

The effect of DPA on cell cycle progression in three colon cancer cell lines[a]

|  |  | Colo 205 | | | HT-29 | | | HCT-15 | | |
|---|---|---|---|---|---|---|---|---|---|---|
|  |  | G0/G1(%) | S(%) | G2/M(%) | G0/G1(%) | S(%) | G2/M(%) | G0/G1(%) | S(%) | G2/M(%) |
|  | 4 μM | 71.6 | 18.1 | 10.4 | 84.1 | 7.4 | 8.5 | 30.5 | 55.3 | 14.3 |
|  | 8 μM | 70.6 | 24.1 | 5.2 | 79.5 | 10.6 | 10.0 | 37.5 | 54.9 | 7.6 |
| 72 h | Control | 62.0 | 28.1 | 9.8 | 75.9 | 17.6 | 6.5 | 58.0 | 32.1 | 9.8 |
|  | 1 μM | 60.3 | 29.6 | 10.1 | 72.6 | 20.1 | 7.3 | 51.8 | 35.0 | 13.2 |
|  | 2 μM | 87.1 | 7.8 | 5.1 | 67.3 | 29.9 | 2.9 | 49.2 | 36.6 | 14.3 |
|  | 4 μM | 76.3 | 13.4 | 10.3 | 86.0 | 8.0 | 6.1 | 40.8 | 42.1 | 17.2 |
|  | 8 μM | 70.7 | 25.8 | 3.4 | 86.3 | 7.5 | 6.2 | 38.2 | 49.9 | 11.9 |

[a]The cell cycle progression of Colo205, HT29 and HCT-15 cells was examined after exposure to DPA for 24, 48 or 72 h.
[b]Each data are the mean of duplicate sample from one of three independent experiment.

Accordingly, the present invention provides in vitro and in vivo anticancer profile of diaminophenyladamantane derivatives. 2,2-Substituted adamantane derivatives exhibited stronger growth inhibitory on anticancer activities in vitro than the corresponding 1,3-substituted analogues. DPA and 1,3-DPA/OH/NH$_2$ were potent growth inhibitory of cancer cell lines in vitro. DPA also exerted G$_0$/G$_1$ cell-cycle arrest without concomitant apoptosis on Colo 205 and HT 29 colon cancer cells. The result was similar to that of DPD (Br. J Cancer 2003; 89:1995-2003). In other words, the induced-G$_1$ arrest without concomitant apoptosis on Colo 205 and HT 29 colon cancer cells is one unique property of DPD or DPA. In addition, the in vivo effect of tumor growth suppression by DPA was also observed on colon Colo 205 xenografts. No acute toxicity was observed after an intraperitoneal challenge of DPA in ICR nude mice weekly. The present invention provides DPA to be a new potentially less toxic modality of cancer therapy.

The present invention not only provides the diaminophenyladamantane derivatives for inhibiting the growth of tumor cells, but also provides a pharmaceutical composition including the diaminophenyladarnantane derivative and the chemotherapeutic agent CPT-11.

Figure 4A:
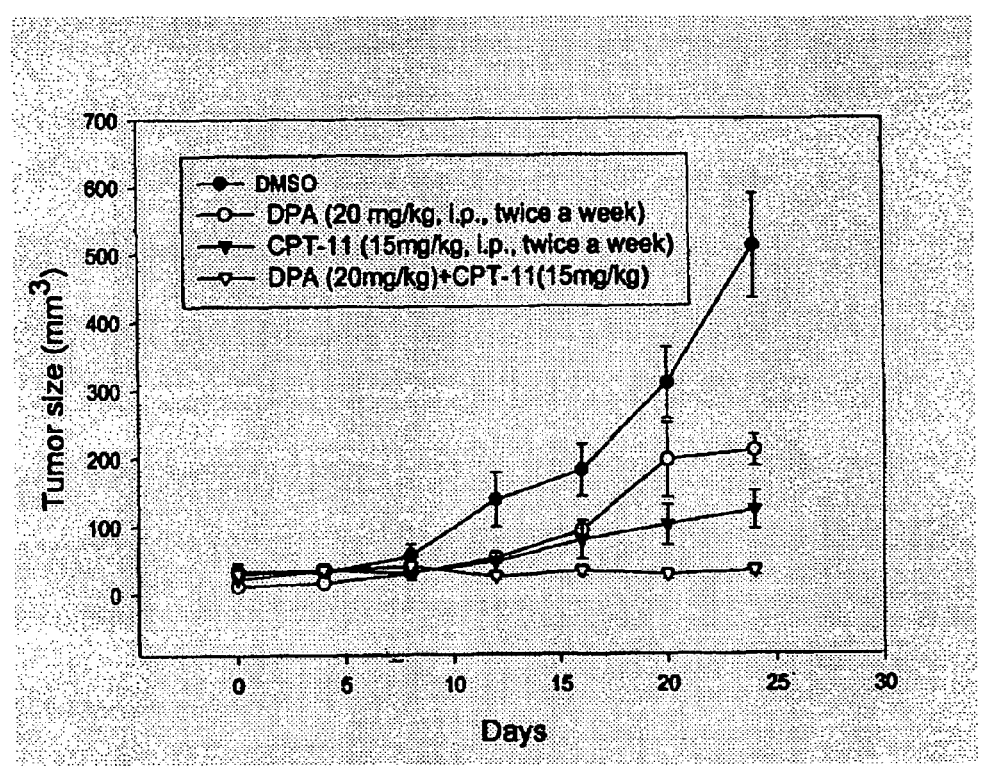
FIG. 4A is a chart showing the in vivo antiproliferation effect of DPA and/or CPT-11 for human colon cancer Colo 205 xenografts.
Figure 4B:
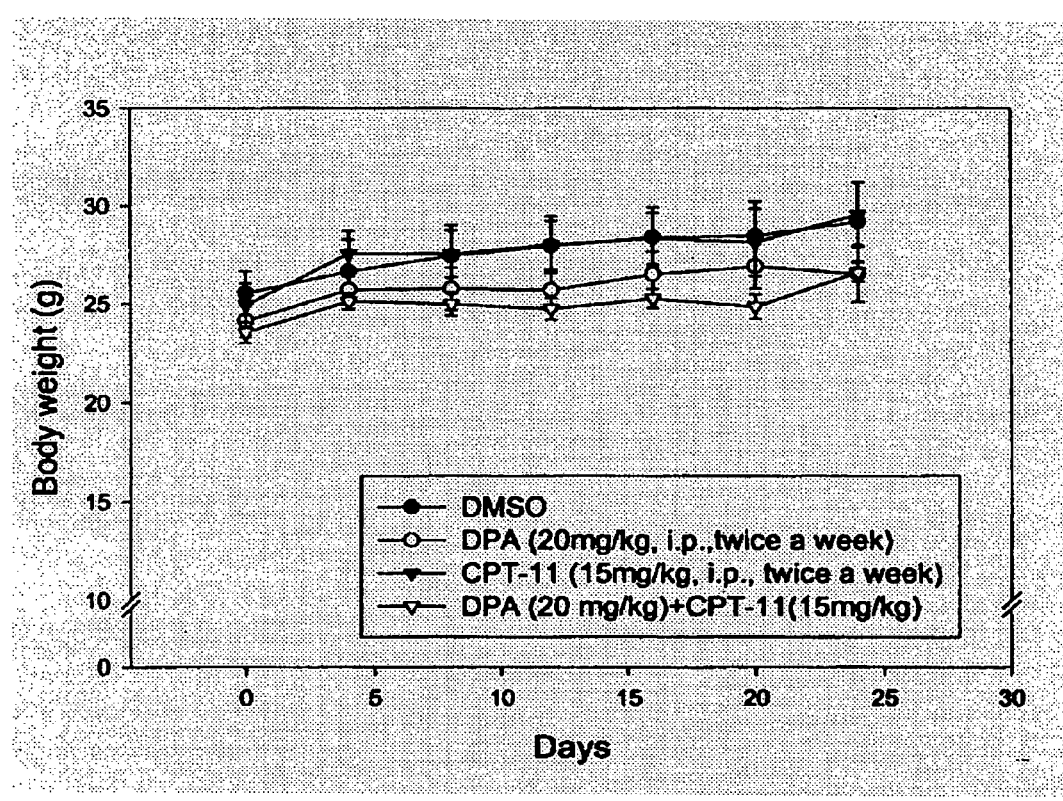
FIG. 4B is a chart showing the change in body weight of nude mice after treatment with DPA and/or CPT-11.

DPA Enhance the In Vivo Antitumor Effect of CPT-11 in Human Colon Cancer Xenografts Previous studies indicated that DPA exhibit in vivo antitumor effect in colon cancer Colo 205 cells xenografts. To further investigate whether DPA could enhance the antitumoral activity of the chemotherapeutic agent CPT-11, Colo 205 cells were treated with DPA or DPA in combination with CPT-11. Cancer cells were transplanted into ICR nude mice, and when the tumors were palpable (30~35 mm$^3$), the mice were treated either with vehicle control, CPT-11 or DPA (20 mg/kg, i.p., twice a week). Tumour volume(V) was calculated according to the following formula: V(mm$^3$)=0.4AB$^2$, where A and B are the longest diameter and the shortest diameter, respectively (Cancer Res. 1966; 26:1787-1800). Treatment of nude mice with DPA(20 mg/kg), the tumor size was significantly (P<0.05) decreased in mice as compared to control groups at the end of experiment. As shown in FIG. 4A the tumor size of control animals had an average of 510 mm$^3$ at the end of this study. In contrast, the tumor size from DPA (20 mg/kg) combined with CPT-11 (15 mg/kg)-treated animals had an average of only 33.6 mm$^3$. The tumor size of DPA in combination with CPT-11-treated mice was a 73% decrease as compared with that of CPT-11-treated mice. From a practical point of view, the antitumoral activity of DPA combined with CPT-11 showed an increase (3.6- to 6.2-fold) in Colo 205 cells as compared with CPT-11 or DPA, alone. These results clearly showed that DPA enhanced the antitumoral activity of the chemotherapeutic agent CPT-11. In addition, the challenge of DPA (20~80 mg/kg, i.p., twice a week) in ICR nude mice produced no obviously acute toxicity. Referring to FIG. 4B, no significant reduction in body weight was found in DPA-treated mice. In addition, no tissue damage was observed in liver, lung and kidney after examination of the tissue slices stained with haematoxylin and eosin.

According to the foregoing experiments, the present invention provides a bis(o-nitrophenol) compound of the formula (I), a bis(o-aminophenol) compound of the formula (II) and the preparation method therefor, and moreover the present invention provides a pharmaceutical composition for inhibiting the growth of tumor cells.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A bis(o-nitrophenols) compound of a formula (I):

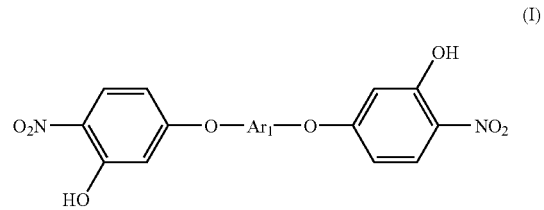

wherein Ar$_1$ is one selected from a group consisting of

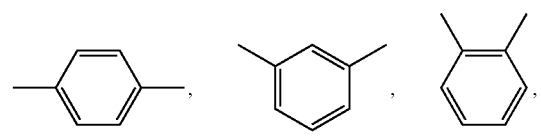

-continued
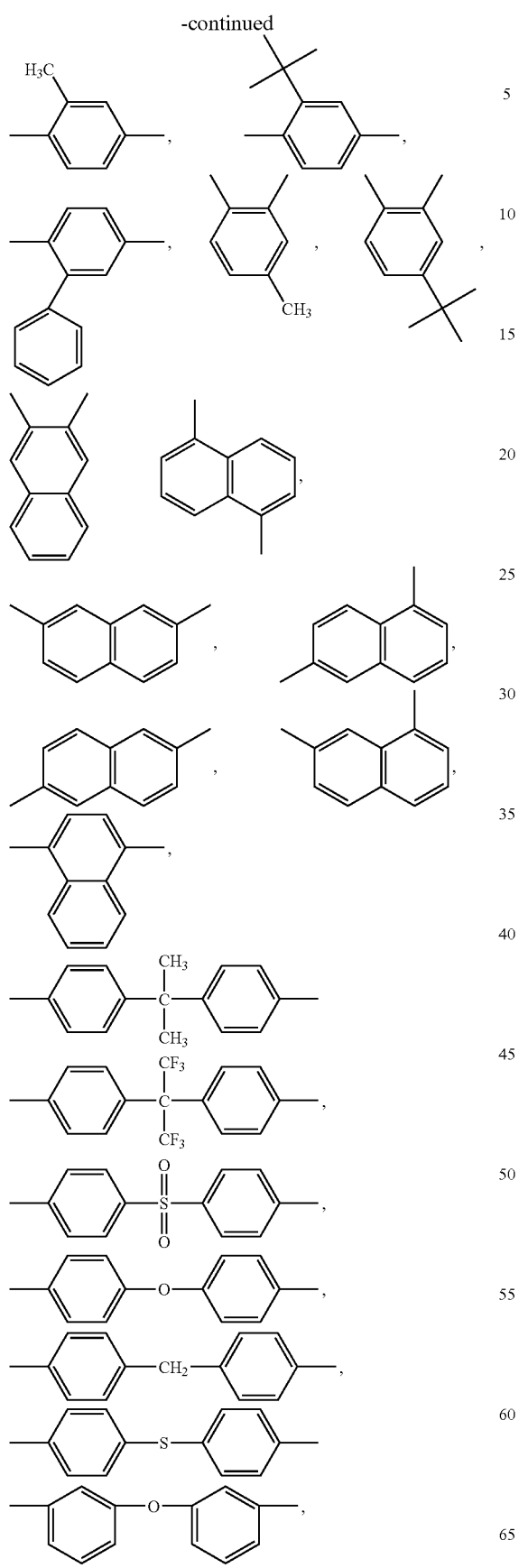
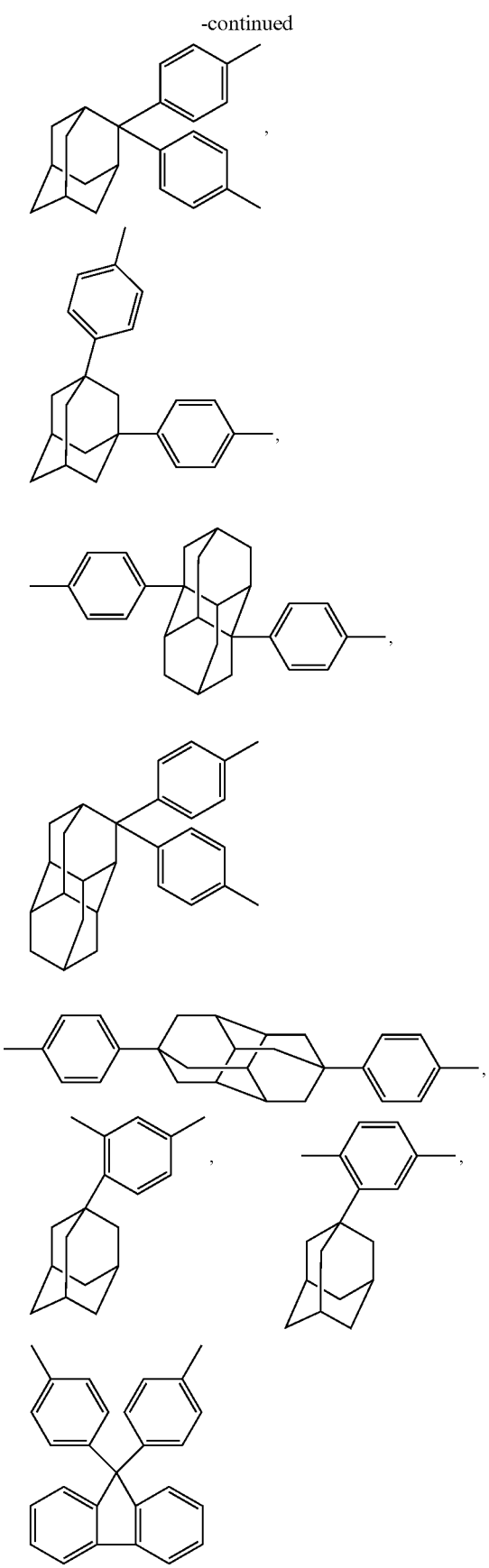

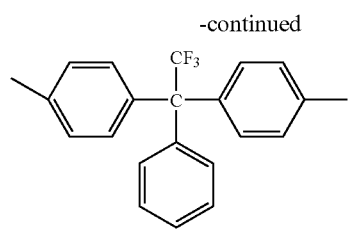
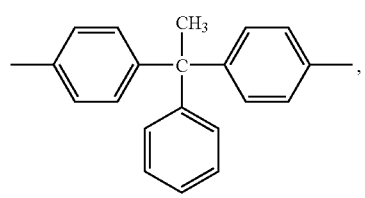
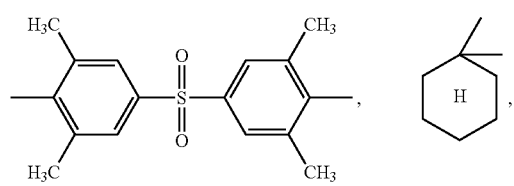
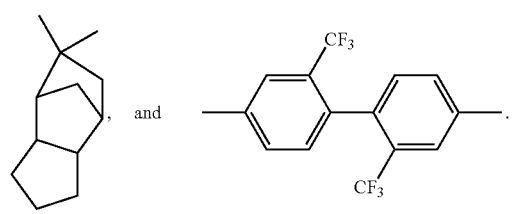
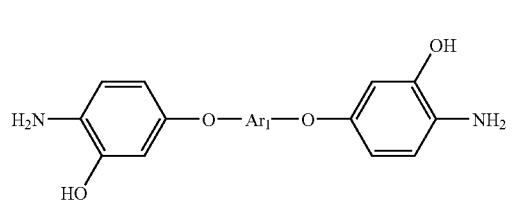
2. A bis(o-aminophenols) compound of a formula (II):
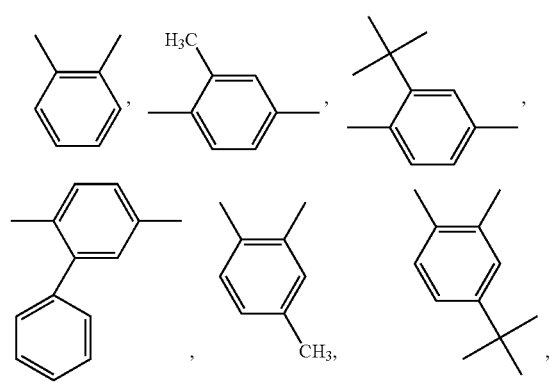
wherein Ar$_1$ is one selected from a group consisting of:
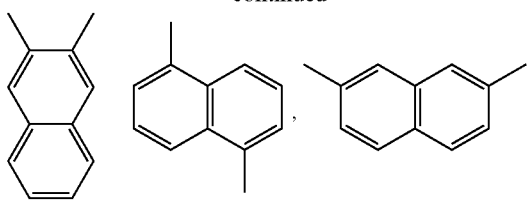
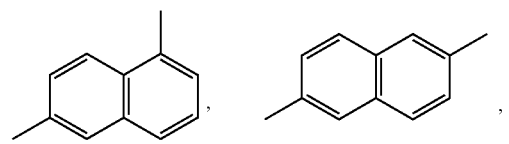
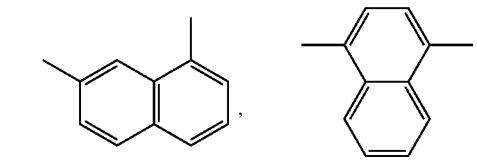
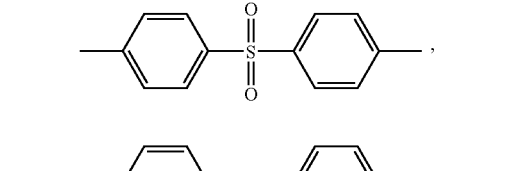
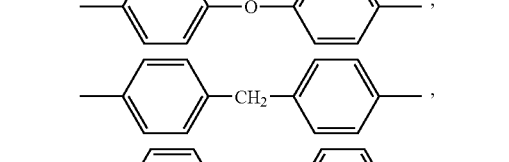
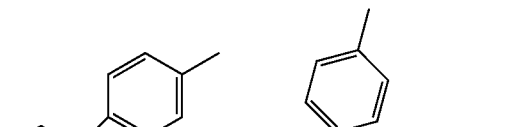
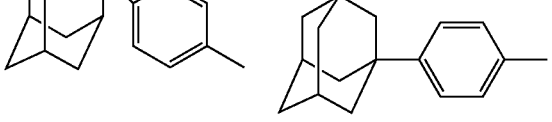
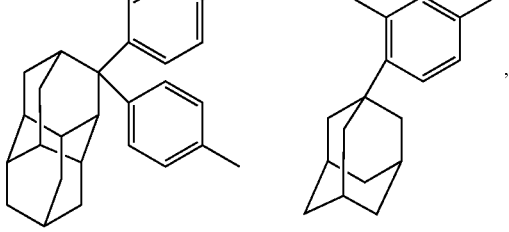

-continued

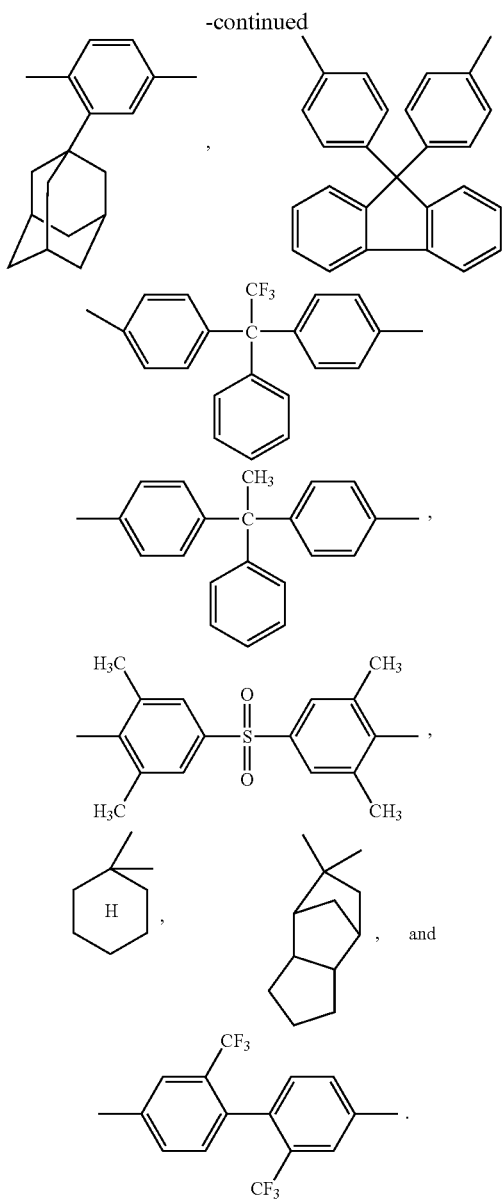

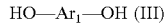

3. A method for preparing a compound of said formula (I) as claimed in claim 1, comprising a step of:
reacting an aromatic diol with at least one 5-halo-2-nitrophenol in the presence of at least one inorganic base in an organic solvent,
wherein said aromatic diol has a formula (III):

HO—Ar₁—OH (III)

wherein Ar₁ is defined as said formula (I) claimed in claim 1.

4. The method according to claim 3, wherein said step is performed at a temperature ranged from 100 to 220° C., and an equivalent ratio of said inorganic base and said aromatic diol is less than 3.

5. The method according to claim 3, wherein said 5-halo-2-nitrophenol is one selected from a group consisting of 5-fluoro-2-nitrophenol, 5-chloro-2-nitrophenol, 5-bromo-2-nitrophenol and a combination thereof.

6. The method according to claim 3, wherein said organic solvent is one selected from a group consisting of N,N-dimethylformamide, N,N-dimethylacetamide, dimethyl sulfoxide, 1-methyl-2-pyrrolidone and a combination thereof.

7. The method according to claim 3, wherein said inorganic base is one selected from a group consisting of a carbonate salt, a hydroxide salt, a fluoride salt and a combination thereof.

8. A pharmaceutical composition for inhibiting a growth of tumor cells, comprising: a compound of formula (II):

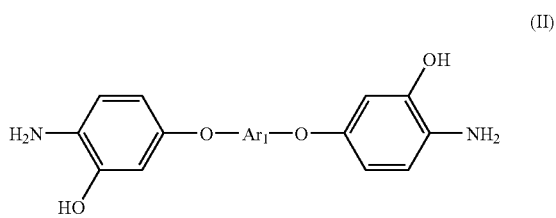

wherein Ar₁ is one selected from a group consisting of:

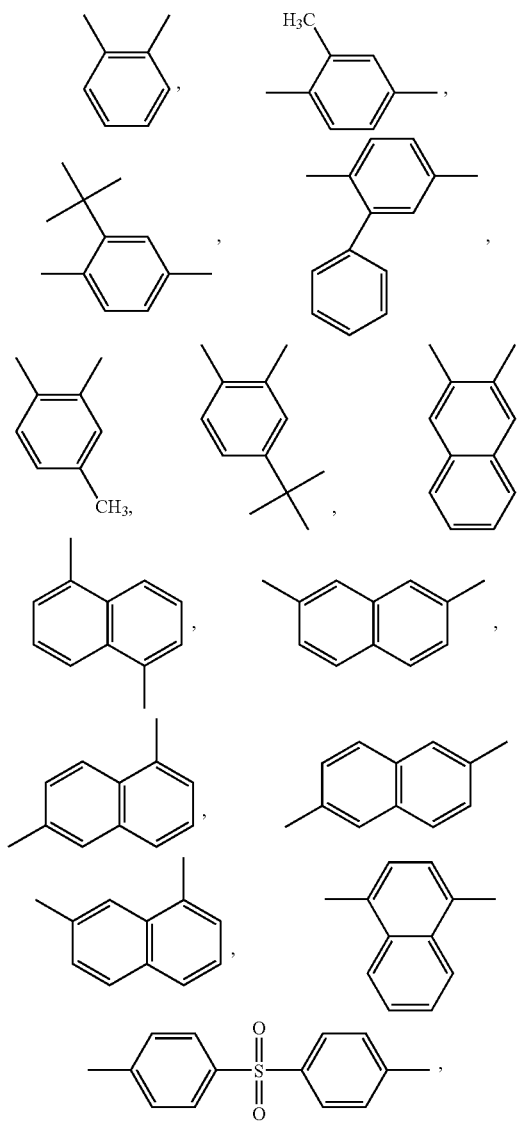

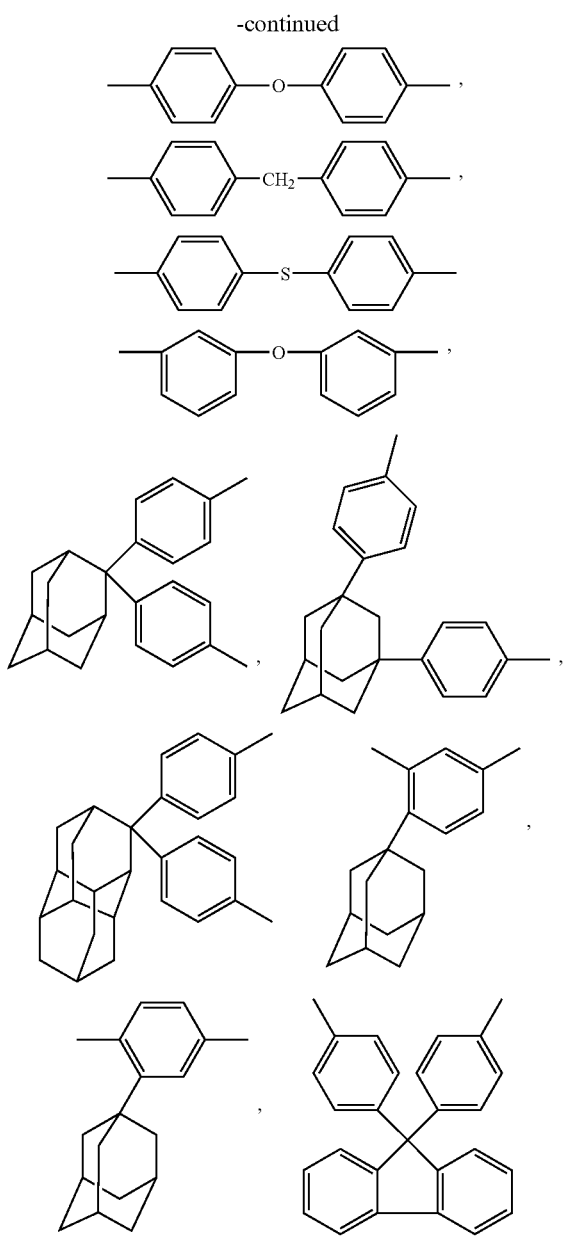
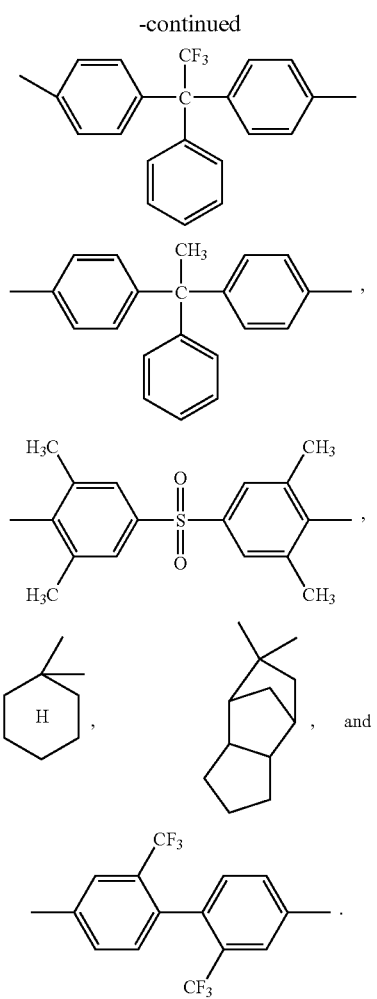
9. The pharmaceutical composition according to claim 8, wherein said compound is 2,2-bis(4-(4-amino-3-hydroxyphenoxy)phenyl)adamantane.
10. The pharmaceutical composition according to claim 8, wherein said compound is 1,3-bis(4-(4-amino-3-hydroxyphenoxy)phenyl)adamantane.
* * * * *